US008546348B2

(12) United States Patent
Huang et al.

(10) Patent No.: US 8,546,348 B2
(45) Date of Patent: *Oct. 1, 2013

(54) UPREGULATION OF OPIOID RECEPTORS FOR MANAGEMENT

(75) Inventors: Li-Yen Mae Huang, Galveston, TX (US); Yanping Gu, League City, TX (US)

(73) Assignee: The Board of Regents of the University of Texas System, Austin, TX (US)

(*) Notice: Subject to any disclaimer, the term of this patent is extended or adjusted under 35 U.S.C. 154(b) by 349 days.

This patent is subject to a terminal disclaimer.

(21) Appl. No.: 12/924,738

(22) Filed: Oct. 4, 2010

(65) Prior Publication Data

US 2011/0091425 A1 Apr. 21, 2011

Related U.S. Application Data

(63) Continuation-in-part of application No. 12/002,307, filed on Dec. 14, 2007, now Pat. No. 7,807,651, which is a continuation of application No. 10/852,593, filed on May 24, 2004, now abandoned.

(60) Provisional application No. 60/472,515, filed on May 22, 2003.

(51) Int. Cl.
*A01N 43/04* (2006.01)
*A01N 43/42* (2006.01)
*C12Q 1/68* (2006.01)
*C12N 15/00* (2006.01)

(52) U.S. Cl.
USPC ............ 514/44 R; 514/289; 435/6; 435/320.1

(58) Field of Classification Search
USPC .................. 514/44 R, 289; 436/6, 320.1
See application file for complete search history.

(56) References Cited

U.S. PATENT DOCUMENTS

| 6,083,386 A | 1/1982 | Lloyd | |
|---|---|---|---|
| 5,824,837 A * | 10/1998 | Chen et al. | 800/3 |
| 6,245,121 B1 | 6/2001 | Lamy et al. | |
| 6,409,788 B1 | 6/2002 | Sower | |
| 6,464,875 B1 | 10/2002 | Woodruff | |
| 7,214,534 B2 | 5/2007 | Law et al. | |
| 2002/0147170 A1 * | 10/2002 | Kopin et al. | 514/44 |
| 2003/0005476 A1 * | 1/2003 | Allen | 800/18 |
| 2007/0016968 A1 * | 1/2007 | Kyrkanides et al. | 800/14 |

OTHER PUBLICATIONS

Hallenbeck. Palliative Care Perspectives. Chapter 4: Types of Pain. London: Oxford University Press, 2003.*
Tomasoni and Benigni. Current Gene Therapy 4: 115, col. 1 lines 4-7, 2004.*
Gautam et al. Am J Respir Med, 1(1):35-46, 2002.*
Yang. Radiology 228:36-49, 2003.*
Zhang et al. Neuroscience 85(1):281-291, 1998.*
Gu et al. Program No. 614.9, 2001 Abstract viewer/Itinerary Planner, Washington, DC: Society for Neuroscience. 2001. Online. http://sfn.scholarone.com/itin2001/.*
Gu et al., 2005 Journal of Pain 6(7):447-454
Xu et al., 2003, Proc Natl Acad Sci 100(10):6204-6209.
Xu et al., 2003, Hum Gen Ther 14(9):897-906.
Tomasoni and Benigni. Current Gene Therapy 4:115, col. 1 lines 4-7, 2004.
Guatam et al. Am J Respir Med, 1(1): 35-46, 2002.
Yang. Radiology, 228(1): 36-49, 2003.
Zhang et al. Neuroscience 85(1): 281-291, 1998.
Gu et al. Program No. 614.9, 2001. Abstract viewer/Itinerary Planner, Washington, DC: Society for Neuroscience. 2001. Online. http://sfn.scholarone.com/itin2001/.
Glatzel et al. PNAS 97(1). 442-447, 2000.
Kabli and Cahill, Pain, 127:84-93 (2007).
Wu et al. Gene Ther., 9(4):245-255 (2002).
Thompson et al. Neuron, 11 (5):903-913 (1993).
Huang et al. Neuron, 17(1):135-45 (1996).
Hargreaves et al. Pain, 32(1):77-88 (1988).

* cited by examiner

*Primary Examiner* — Marcia S Noble

(57) ABSTRACT

Disclosed are methods for treating pain in a subject. The method includes upregulating expression of opioid receptors in the subject's dorsal root ganglion or trigeminal neurons. Also disclosed are methods of treating neuropathic and/or chronic pain in a subject. The method includes upregulating expression of μ-opioid or δ-opioid receptors in the subject's dorsal root ganglion or trigeminal neurons.

2 Claims, 13 Drawing Sheets

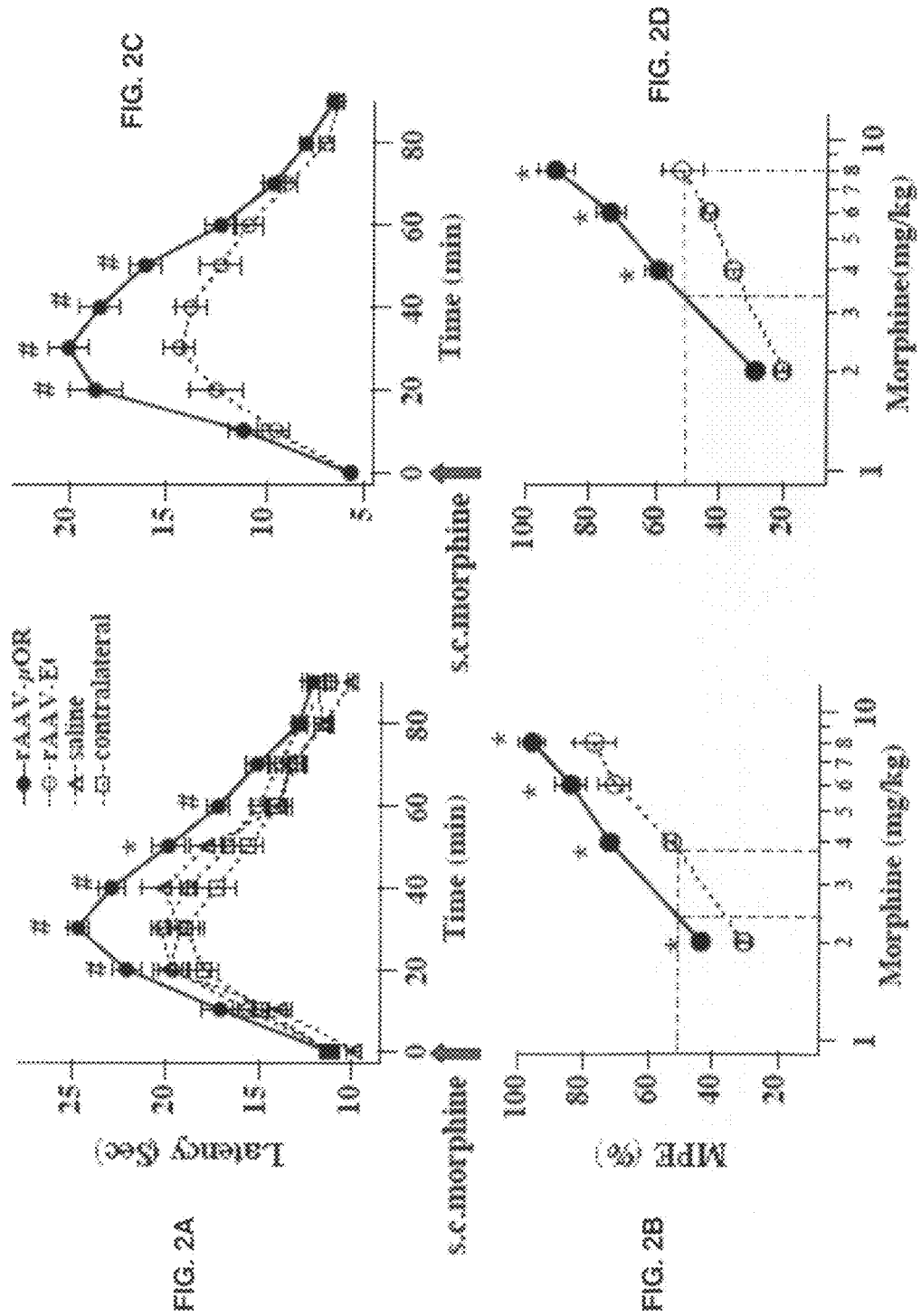

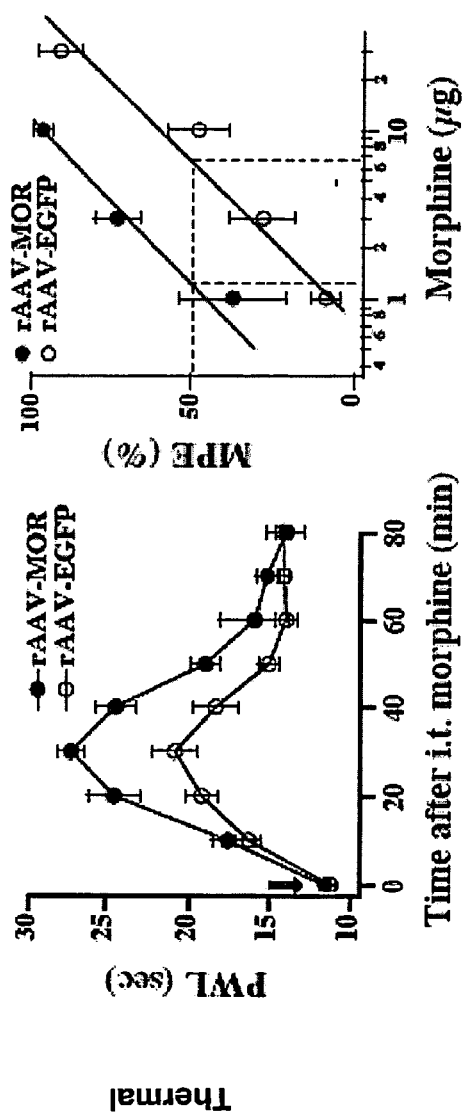
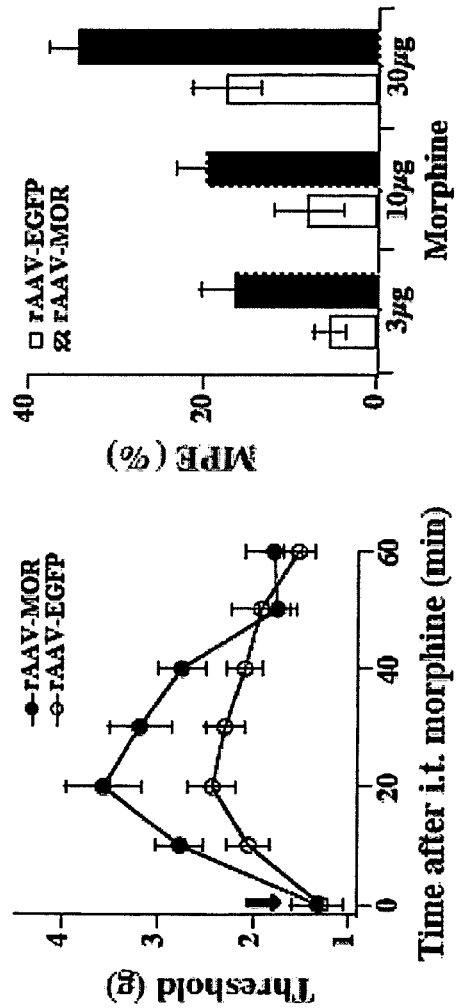
FIG. 8A
FIG. 8B

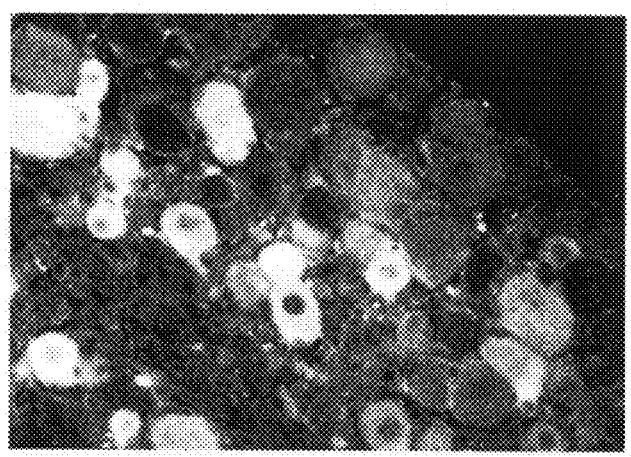
FLAG          FIG. 10A
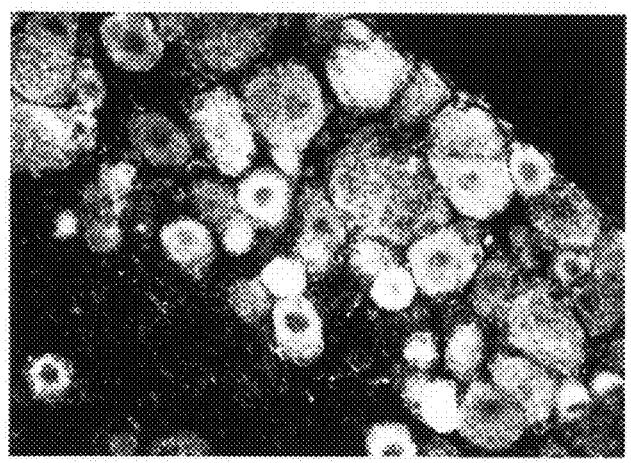
DOR          FIG. 10B
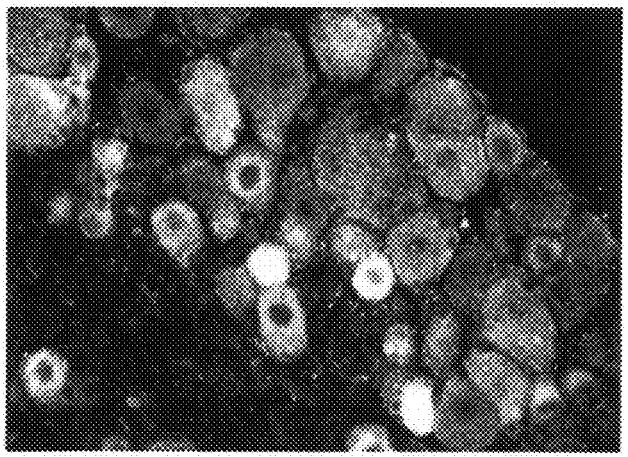
Merge          FIG. 10C

UPREGULATION OF OPIOID RECEPTORS FOR MANAGEMENT

CROSS-REFERENCE TO RELATED APPLICATION

This is a continuation-in-part of application U.S. Ser. No. 12/002,307, filed Dec. 14, 2007, which is a continuation of non-provisional application U.S. Ser. No. 10/852,593, filed May 24, 2004, now abandoned, which claims the benefit of provisional application U.S. Ser. No. 60/472,515, filed May 22, 2003, now expired, the entirety of all of which are hereby incorporated by reference.

FEDERAL FUNDING LEGEND

The present invention was made with the support of the National Institutes of Health Grant Nos. NS30045, NS11255, and DA13668. Consequently, the Federal Government may have certain rights in this invention.

BACKGROUND OF THE INVENTION

1. Field of the Invention

The present invention is directed, generally, to methods and materials for pain management and, more particularly, to methods and materials for pain management by increasing the antinociceptive effect of opioids.

2. Description of the Related Art

Chronic pain is a common complaint of patients who undergo surgical procedures or suffer from long term illness, including cancer, nerve injury, arthritis, or heart disease. Pharmacological agents used for treating chronic pain are often unsatisfactory because of the side effects accompanied the treatment. For example, opiates, at high doses, are apt to produce sedation, respiratory depression and tolerance, which severely limit their use. Recently, genetic approaches have been attempted to manage the chronic pain. One strategy is to increase the production of endogenous μ-opioid receptor ligands by introducing opioid precursor genes for enkephalin and β-endorphin into DRG neurons or meninges surrounding the spinal cord through adeno- or herpes viral vectors. The enhancement of opioid peptides effectively reduces nociceptive behaviors in rats. So far the success of this approach has been limited by several including transient expression of the target genes and potential possibilities of tolerance development as result of upregulation of opioids.

Furthermore, while there are many studies addressing the δ-opioid receptors (DOR) expression following nerve injury, the findings are quite conflicting. Differences in d-opioid receptor agonists or antibodies used in the studies contribute to the confusing results. The most recent and relevant finding is the study of Kabli and Cahill (1) who show that following sciatic nerve ligation, δ-opioid receptor expression increases on both ipsi- and contralateral side of the ligation. In addition, morphine is effective for 14 days and the d-opioid receptor agonist, deltorphin, is effective for 21 days in reducing allodynic responses in injured rats. The study cannot explain why morphine and deltorphin are rather ineffective in reducing allodynia responses in nerve-injured rats when compared with normal rats. More importantly, Kali and Cahill's finding did not suggest any benefit would be derived by an increase in δ-opioid receptor expression in dorsal root ganglions. Thus, there remains a need to more effectively manage chronic pain by increasing the antinociceptive effect of opioids. The present invention fulfills this long-standing need in the art by increasing levels of opioid receptors in neurons by the administration of nucleic acid constructs.

SUMMARY OF THE INVENTION

The present invention relates to a method of treating pain in a subject, said method comprising increasing levels of opioid receptors in the subject's neurons. Although a person having ordinary skill in this art would recognize that the methods described herein may used with a variety of nerve bundles, preferably the neurons are dorsal root ganglion neurons or trigeminal sensory neurons. Preferably, the opioid receptors increased are either μ-opioid or δ-opioid receptors. Various types of pain may be treated using these methods with representative examples including neuropathic pain and chronic pain.

In the methods of the present invention, increasing levels of opioid receptors may be achieved by contacting the subject's neurons with a non-endogenous nucleic acid molecule construct encoding an opioid receptor such as a μ-opioid or δ-opioid receptor. The nucleic acid molecule construct may comprise a vector or is a naked DNA construct. Representative vectors include but are not limited to adeno-associated virus vectors or bacterial vectors. The vector comprises a gene encoding a μ-opioid receptor or δ-opioid receptor under the control of a promoter. The promoter may be a neuron specific promoter or a viral promoter such as a human cytomegalovirus promoter or others that are well known in the art. In a preferred aspect, the nucleic acid molecule construct expresses opioid receptor in the subject's nerve or neurons. Representative nerves or neurons for injection include the dorsal root ganglion neurons, trigeminal sensory neurons, the sciatic nerve, or the trigeminal nerve. In a particularly preferred embodiment, the methods of the present invention further comprises administering an opioid to the subject. For example, the nucleic acid molecule construct may be administered once at the beginning of a treatment period, and the opioid may be administered over the course of the treatment period. In one aspect, the treatment period is more than about 1 week, about 2 weeks, about 1 month, about 2 months or about 6 months.

BRIEF DESCRIPTION OF THE DRAWINGS

FIGS. 2A-2D are graphs showing that morphine antinociceptive effects are enhanced in rAAV-μOR injected rats. FIG. 2A shows the paw withdrawal latencies (PWLs) after the treatment of 4 mg/kg morphine in non-CFA (uninflamed) rats. The antinociceptive effects reached a maximum by 30-40 min and then gradually dissipated in 80-90 min. The PWLs obtained from the rat paw ipsilateral to the rAAV-EGFP (open circles; n=12) or normal saline (open triangles; n=6) injection or from the paw contralateral to the rAAV-μOR injection (open squares; n=6) were all similar. In contrast, the paw withdrawal latencies obtained from the paw ipsilateral to the rAAV-μOR injection (filled circles; n=10) were larger, suggesting an enhanced antinociceptive effect of morphine. FIG. 2B shows the morphine dose-response curves for non-CFA rats injected with rAAV-EGFP or rAAV-μOR. For all morphine doses, the antinociceptive responses of morphine, expressed in MPEs, in rAAV-μOR rats were significantly enhanced (n=5). FIGS. 2C and 2D show that, in CFA (inflamed) rats, the antinociceptive effect of morphine in rAAV-μOR rats was even more enhanced. The paw withdrawal latencies obtained from rAAV-mOR rats (filled circles; n=5) were much larger than those from rAAV-EGFP rats (open circles; n=5). *, $P<0.05$; #, $P<0.01$.

FIG. 3C shows dose dependence of $Ca^{2+}$ channel inhibition by DAMGO after rAAV-μOR infection. The $Ca^{2+}$ channel currents were measured at different concentrations of DAMGO. Cells insensitive to DAMGO were not included in the analysis. Data were fit with the Hill equation with Hill coefficient=1. The maximal inhibition for rAAV-μOR cells was 31.63%, which was significantly larger than that for untreated and rAAV-EGPF cells (about 22%). The $IC_{50}$ for rAAV-μOR cells was 3- to 4-fold smaller than for control cells. The data were obtained from 3 to 24 cells.

FIG. 6A shows the antinociceptive responses of morphine (8 mg/kg), expressed in maximum possible effects (MPEs), in CFA-treated rats injected with either rAAV-μOR (filled circles) or rAAV-EGFP (open circles) into the L4-L5 DRGs. The antinociceptive effects reached a maximum around 30-40 min and then slowly dissipated in 100 min. The MPEs obtained from the paw ipsilateral to rAAV-μOR injection (n=6) were larger (*$P<0.05$; #$P<0.01$) than those obtained from the paw ipsilateral to rAAV-EGFP injection (n=5). FIG. 6B shows the antinociceptive responses of morphine (10 mg/kg) in inflamed rats after either rAAV-μOR (filled circles) (n=4) or rAAV-EGFP (open circles)) (n=4) was injected into the sciatic nerves. The antinociceptive responses of morphine in rAAV-μOR rats were significantly higher than those in rAAV-EGFP rats.

FIG. 8A is a graph showing the time courses of morphine effects following intrathecal (i.t.) administration of 10 μg morphine in nerve ligated rats with and without rAAV-μOR treatment. FIG. 8B is a dose response curve of morphine effects following intrathecal (i.t.) administration of 1-10 μg morphine in control rats and in rAAV-μOR rats.

FIGS. 8A-8B is a graph showing the morphine effects on thermal (FIG. 8A) or mechanical Von Frey (FIG. 8B) stimulation following intrathecal (i.t.) administration of 1-10 μg morphine in spared nerve injury rats with and without rAAV-μOR treatment. The time courses of morphine effects are shown on the left and the dose response curves of morphine effects are on the right.

FIGS. 10A-10C shows FLAG-labeled DRG neurons are d-opioid receptor positive. An antibody against d-opioid receptors was used to label DRG neurons isolated from injected rats. All of the FLAG-labeled cells were δ-opioid receptor-positive. Bar scale=25 μm.

(FIG. 12A) The dose-response of deltorphin for allodynic behavioral responses was determined in spared nerve injury (SNI) rats and in SNI rats treated with rAAV-δOR. Intrathecal deltorphin was rather ineffective in reducing allodynic responses in SNI rats, but became effective in rAAV-δOR treated SNI rats. (FIG. 12B) The efficacy increased by 3.4-fold whereas the potency of deltorphin did not change significantly.

(FIG. 13A). The dose-response of morphine for allodynic behavioral responses was determined. The effectiveness of morphine in reducing allodynic behaviors in SNI rats was significantly increased after rAAV-dOR treatment (FIG. 13B). The efficacy of morphine increased by 5.1-fold and the potency increased by 40-fold.

DETAILED DESCRIPTION OF THE INVENTION

Figure 1A:
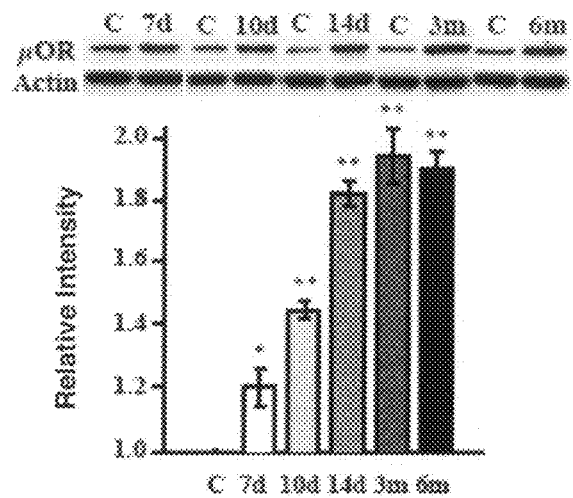
FIGS. 1A and 1B are images of Western blots and associated bar graphs showing μ-opioid receptor (μOR) expression upregulation in the dorsal root ganglion (DRG) and spinal cord in accordance with a method of the present invention. L4 and L5 DRGs (FIG. 1A) and the dorsal spinal cord (FIG. 1B) ipsilateral to the rAAV injection were removed from animals at various times and the expression of μORs was probed with the anti-μOR antibody. The intensities of protein bands (about 51 kDa) were normalized with actin in the sample. The μOR expression on the contralateral side (C) was set at 1.0. The μOR expression in DRG cells increased with time and approached a plateau of about 2-fold 14 days after infection. The μOR expression in the spinal cord reached a maximum of 1.5-fold. The expression in both DRGs and the spinal cord remained stable for at least 6 months (*, P<0.05; **, P<0.01).

The present invention relates to a method of treating pain in a subject by upregulating expression of opioid receptors in the subject's dorsal root ganglion neurons.

"Pain" as used herein, is meant to include, for example, chronic and/or neuropathic pain, such as pain related to long term illness, pain related to cancer or cancer treatment, pain related to arthritis, pain related to heart disease, pain related to injuries to the nervous system, pain related to spinal cord injury, pain related to diabetes, pain related to chronic inflammation, and/or pain related to loss of a limb.

"Subject", as used, herein is meant to include mammals, such as mice, rats, cats, dogs, sheep and humans and other primates. The subject can be one who suffers from chronic pain and/or neuropathic pain. Such chronic pain and/or neuropathic pain can be accompanied by mechanical allodynia or not.

"Treating pain", as used herein, is meant to include, for example, the complete elimination of pain as well as any reduction in the severity, duration, and/or frequency of pain, for example, a reduction in the severity, duration, and/or frequency of pain by at least about 10%, such as by at least about 20%, by at least about 30%, by at least about 40%, by at least about 50%, by at least about 60%, by at least about 70%, by at least about 80%, by at least about 90%, as measured for an individual or for a group of individuals by any objective or subjective test for pain that is recognized as such by one skilled in the art or that may become recognized as such by one skilled in the art. For example, in subjects suffering from chronic pain and/or neuropathic pain that is accompanied by mechanical allodynia, reduction in the severity, duration, and/or frequency of pain can be assessed using Von Frey hairs, for example, as described in Boivie et al., eds, *Touch, Temperature, and Pain in Health and Disease: Mechanisms and Assessments*, Seattle: IASP Press (1994), which is hereby incorporated by reference.

"Dorsal root ganglion neurons", as used herein, are meant to include, for example, neurons of the lumbar dorsal root ganglia, large dorsal root ganglion neurons (i.e., dorsal root ganglion neurons having a diameter of greater than about 35 μm), medium dorsal root ganglion neurons (i.e., dorsal root ganglion neurons having a diameter of greater than about greater than about 25 μm but less than about 35 μm), small dorsal root ganglion neurons (i.e., dorsal root ganglion neurons having a diameter of less than about 25 μm), myelinated and unmyelinated dorsal root ganglion neurons. The dorsal root ganglion neurons include those which express endogenous μ-opioid receptors and/or endogenous δ-opioid receptors as well as those which do not express endogenous μ-opioid receptors and/or endogenous δ-opioid receptors.

"Trigeminal ganglion neurons" are used herein, are meant to include for example, neurons of large trigeminal neurons (i.e., trigeminal ganglion neurons having a diameter of greater than about 35 μm), medium trigeminal ganglion neurons (i.e., trigeminal ganglion neurons having a diameter of greater than about greater than about 25 μm but less than about 35 nm), small trigeminal ganglion neurons (i.e., trigeminal ganglion neurons having a diameter of less than about 25 μm), myelinated and unmyelinated trigeminal ganglion neurons. The trigeminal ganglion neurons include those which express endogenous μ-opioid receptors and/or endogenous δ-opioid receptors as well as those which do not express endogenous μ-opioid receptors and/or endogenous δ-opioid receptors.

"Opioid receptors", as used herein, are meant to include δ-opioid receptors, K-opioid receptors, and δ-opioid receptors, as well as combinations thereof.

As used herein, "upregulating the expression of opioid receptors" is meant to include any form of non-endogenous expression of opioid receptors.

Expression of opioid receptors can be upregulated by contacting the dorsal root ganglion neurons or trigeminal ganglion neurons with a non-endogenous nucleic acid molecule construct encoding a μ-opioid receptor or other opioid receptor under conditions effective to cause the nucleic acid molecule to express the μ-opioid receptor or other opioid receptor in the dorsal root ganglion neurons or trigeminal ganglion neurons. Illustratively, such constructs can include a nucleic acid molecule encoding a μ-opioid receptor coupled to a suitable expression vector, such as a plasmid or viral vector, and such constructs can be prepared by any suitable method, for example, using the recombinant techniques described in Maniatis et al., Molecular Cloning: A Laboratory Manual, Cold Springs Laboratory, Cold Springs Harbor, N.Y. (1982), which is hereby incorporated by reference.

Expression of the μ-opioid receptor or other opioid receptor can be carried out via the nucleic acid molecule construct itself (e.g., as in the case where the plasmid or viral vector containing the nucleic acid molecule encoding the μ-opioid receptors or d-opioid receptors is itself involved in the expression), or expression of the μ-opioid receptor or d-opioid receptor can be carried out by having the nucleic acid molecule construct transduce the dorsal root ganglion or trigeminal ganglion neurons and having μ-opioid receptor or d-opioid receptor expression carried out not via the nucleic acid molecule construct but, instead, via the transduced dorsal root ganglion neuron or its progeny or trigeminal ganglion neuron or its progeny. In cases where the latter mechanism of expression is desired, transduction can be carried out, for example, using an adeno-associated virus ("AAV") vector, such as an adeno-associated virus vector which includes a gene encoding a μ-opioid receptor or a δ-opioid receptor under control of a neuron-specific endolase promoter.

Methods for preparing adeno-associated virus vectors capable of transducing dorsal root ganglion neurons with nucleic acid molecule encoding opioid receptors are described herein. Further details regarding these preparative methods can be found in Xu et al., "Efficiencies of Transgene Expression in Nociceptive Neurons Through Different Routes of Delivery of Adeno-associated Viral Vectors," *Hum. Gene Ther,* 14(9):897-906 (2003), which is hereby incorporated by reference, and in Xu et al., "Adeno-Associated Viral Transfer of Opioid Receptor Gene to Primary Sensory Neurons: A Strategy to Increase Opioid Antinociception," *Proc. Natl. Acad. Sci. U.S.A.,* 100(10):6204-9 (2003), which is hereby incorporated by reference.

Expression of opioid receptors can be upregulated in any or all of the subject's dorsal root ganglion or trigeminal ganglion neurons, such as in the case where expression of opioid receptors are upregulated only in the subject's large dorsal root ganglion or trigeminal ganglion neurons; only in the subject's medium dorsal root ganglion neurons; only in the subject's small dorsal root ganglion or trigeminal ganglion neurons; in the subject's large and medium dorsal root ganglion or trigeminal ganglion neurons; in the subject's large and small dorsal root ganglion neurons; and/or in the subject's large, medium, and small dorsal root ganglion or trigeminal ganglion neurons. Expression of opioid receptors in large dorsal root ganglion neurons which do not endogenously express opioid receptors is particularly surprising and is believed to be, at least in part, responsible for the effectiveness of the present invention in treating neuropathic and/or chronic pain.

As discussed above, expression of opioid receptors in the subject's dorsal root ganglion or trigeminal ganglion neurons is upregulated by contacting the subject's dorsal root ganglion or trigeminal ganglion neurons with a non-endogenous nucleic acid molecule construct encoding a μ-opioid receptor. Contacting of the subject's dorsal root ganglion or trigeminal ganglion neurons with the nucleic acid molecule construct can be carried out by any suitable method. Illustratively, the nucleic acid molecule construct can be administered into a nerve, such as the sciatic nerve or the trigeminal nerve; and/or the nucleic acid molecule construct can be injected directly into the subject's dorsal root ganglia or trigeminal ganglia.

The methods of the present invention can further include administering an opioid to the subject. Examples of opioids that can be administered in the practice of this aspect of the present invention include codeine, fentanyl, hydrocodone, hydromorphone, levorphanol, meperidine, methandone, morphine, oxycondone, oxymorphone, propoxyphene, and combinations thereof. The opioid can be administered in any suitable form and by any suitable route, such as orally, intravenously, or intrathecally. The opioid can be administered in multiple regularly-scheduled bolus doses, continuously, or on an as-needed basis. For example, the opioid can be administered continuously via a transdermal patch (e.g., Durogesic™), or it can be administered on an as-needed basis using a morphine pump.

The opioid can be administered over an extended period of time, such as over about 1 week, over about 2 weeks, over about 1 month, over about 2 months, over about 3 months, over about 4 months, over about 5 months, over about 6 months, etc. in multiple regularly-scheduled bolus doses, continuously, or on an as-needed basis.

In one embodiment of the present invention, the nucleic acid molecule construct is administered once at the beginning of a treatment period, and the opioid is administered over the course of the treatment period. The treatment period can be more than about 1 week, more than about 2 weeks, more than about 3 weeks, more than about 1 month, more than about 2 months, more than about 3 months, more than about 4 months, more than about 5 months, more than about 6 months, or longer. At the end of the treatment period, a new treatment period can be commenced by again administering the nucleic acid molecule construct to the subject and administering the opioid over the course of the treatment period. As should be apparent from the above discussion, in this embodiment of the present invention, during any given treatment period, the nucleic acid molecule construct is administered only once.

The present invention is further illustrated with the following examples.

Example 1

Transfer of Opioid Receptor Gene to Primary Sensory Neurons Increases Opioid Antinociception—Materials and Methods Preparation of rAAV Plasmid Constructs and Viral Stocks The plasmid pTR-NSE and pTR-NSE-enhanced GFP (EGFP) were prepared as described in Wu et al., (2). The MOR-1 gene-containing plasmid pCMV-μOR, prepared in accordance with Thompson et al (3), was used as the template for PCR amplification to insert a SalI site to the 5' end and a 6×His peptide sequence followed by a HindIII site to the 3' end of the μOR gene. The PCR products were digested by SalI and HindIII. The resulting fragment was ligated into the SalI/HindIII sites of pTR-NSE to generate pTR-NSE-μOR. rAAV viral particles were produced in an adenovirus-free system by cotransfecting HEK 293 cells with a rAAV vector plasmid (i.e., pTR-NSE-μOR or pTR-NSE-EGFP), plasmid pXX2, and pXX6 (4). Cells were collected and lysed, and cellular debris was eliminated by centrifugation to gain crude viral solution. The viral solution was fractionated through a Heparin Agarose type I column (Sigma) to yield a purified viral stock.

Infection of Dorsal Root Ganglion ("DRG") Neurons with rAAVs

Primary neuronal cultures were prepared from DRGs of 14-day Sprague-Dawley rats as described in Huang et al. (5). Cells were plated onto coverslips and grown in MEM (GIBCO/BRL) with 10% FBS. To infect cultured DRG neurons, a serum-free medium containing 1 μl of viral solution was added to DRG cultures 24-48 h after plating. Ninety minutes later, additional serum (20%)-containing medium was added. The medium was changed within 24 h and every 2-3 days afterward. For in vivo experiments, 25- to 30-day-old rats were anesthetized with pentobarbital (50 mg/kg), and left L4 and L5 DRGs were exposed. A viral solution (2 μl) containing either rAAV-μOR or rAAV-EGFP was slowly (15-20 min) injected into each ganglion with a Hamilton syringe. The wound was then closed; animals were returned to their cages.

Morphological Analysis

Cultured DRG cells were fixed with PBS containing 4% paraformaldehyde and 0.2% picric acid at 4° C. for 1 h. To obtain tissue sections, injected rats were perfused with the same fixative. DRGs and the spinal cord were then removed and sectioned (10 μm thick) in a cryostat. Morphological integrity of DRGs was examined by staining tissue with hematoxylin/eosin. To detect exogenous μORs, either the monoclonal mouse anti-His antibody (Qiagen, Valencia, Calif., 1:20; for cultured DRGs) or the polyclonal rabbit anti-His antibody (Santa Cruz Biotechnology, 1:200; for tissue sections) was used. Fluorescein anti-mouse or anti-rabbit IgG (Vector Laboratories) was the secondary antibody. A polyclonal anti-μOR antibody (DiaSorin, Stillwater, Minn., 1:200) was used to label endogenous and exogenous μORs, and a rhodamine red-conjugated goat anti-rabbit IgG (Jackson ImmunoResearch) was for visualization. The primary anti-μOR antibody was specific because the antibody pretreated with the μOR peptide immunogen no longer labeled μORs EGFP was visualized without further treatment. Mouse NeuN (Chemicon, 1:200) was used to label neurons. Mouse anti-N52 (Chemicon, 1:200) was used to label myelinated DRGs; mouse anti-periphrin (Chemicon, 1:200) was used to label cells unmyelinated DRGs. Alexa Fluor 546 goat anti-mouse IgG (Molecular Probes, 1:200) was used for visualization. To avoid the possibility of double-counting, labeled cells in every fifth section were counted.

Western Analyses

Total proteins were extracted from DRGs and the spinal cord of injected rats by using the standard methods (6). Protein extracts (10-30 μg) were subjected to SDS/PAGE (10% acrylamide). Proteins were transferred onto nitrocellulose membranes and subsequently incubated with rabbit anti-μOR antibody (DiaSorin, 1:1,000) for μOR detection. Actin, used as an internal control, was labeled with mouse anti-actin antibody (Chemicon, 1:1,000). Blots were detected by using secondary antisera coupled to horseradish peroxidase and developed by using the enhanced chemiluminescence kit (Amersham Biosciences). Blot intensities were analyzed with a LYNX 5000 image analyzer.

Behavioral Tests

Thermal hyperalgesia to radiant heat was assessed as described in (7). Three to four weeks after rAAV injection, rats were acclimated in Plexiglas boxes placed on a platform for 30 min/day for 5 days. To measure paw withdrawal latencies ("PWLs"), a radiant heat source was placed under the plantar surface of the hind paw and the time elapsed from the onset of radiant heat stimulation to the withdrawal of the paw was recorded. The heat intensity was adjusted to give a baseline latency of about 10 s; a cutoff time of 30 s was set to prevent possible tissue damage. To obtain baseline paw withdrawal latencies, three measurements separated by a 5-min interval were made for each rat's hind paw, and scores were averaged. The antinociceptive effects of morphine were evaluated by measuring paw withdrawal latencies before and every 10 min after the s.c. morphine administration. To induce inflammation, rats were lightly anesthetized with pentobarbital. Complete Freund's adjuvant ("CFA") (*Mycobacterium butyricum* from Difco) emulsion (1:1 peanut oil/saline, 1 mg of *Mycobacterium* per ml) was injected into the plantar surface (50 µl) of the rat left hind paw 3-4 weeks after infection of rAAV. Behavioral experiments were performed 5-14 days after the CFA injection.

Perforated Patch Recording

Cells were superfused (2 ml/min) at 23-24° C. with external solution containing 130 mM tetraethylammonium ("TEA") chloride, 5 mM CsCl, 1.5 mM $BaCl_2$, 1 mM $MgCl_2$, 10 mM Hepes, and 10 mM glucose (pH 7.2, adjusted with TEA-OH; osmolarity, 300 mosM). Patch electrodes (resistance, 2.2-3.5 MΩ) were filled with internal solution containing 100 mM $CsMeSO_3$, 40 mM CsCl, 10 mM Hepes, and 300 µg/ml amphotericin B (pH=7.3 adjusted with CsOH, 320 mosM). The currents were filtered at 2-5 kHz and sampled at 100 µs per point. [$D-Ala^2$,$N-MePhe^4$,$Gly^5$-ol]enkephalin ("DAMGO") was pressure delivered to the recorded cells through a drug applicator (8).

Data Analysis

All data were expressed as mean±SEM. Paw withdrawal latencies obtained from different rats were averaged. Changes before and after morphine treatment within one rat group were analyzed with one-way ANOVA followed by post hoc Newman-Keuls analysis. Antinociceptive responses were expressed as maximum possible effect ("MPE") by using the relation MPE=(postdrug PWL−baseline PWL)/(cutoff PWL−baseline PWL)×100. Dose-response curves were plotted as MPE vs. dose and fitted with the logistic equation. The doses estimated to produce 50% MPE, A50, and 95% confidence intervals were determined. The dose-response curves for DAMGO in current measurements were fitted with the Hill equation, i.e., response=(max−min)×[$IC_{50}/(IC_{50}{}^n+dose^n)$]+min, where max and min are maximal and minimal responses, $IC_{50}$ is the dose for 50% of the block, and n is the Hill coefficient. The 95% confidence band analysis was used to evaluate the significance of the change in the $IC_{50}$ and maximal block. To assess the significance of changes between two means, the Student's t test was used. A $p<0.05$ was considered significant.

Example 2

Transfer of Opioid Receptor Gene to Primary Sensory Neurons Increases Opioid Antinociception Stable Enhanced Expression of µORs in DRG Neurons Infected with rAAV Vectors Two rAAV vectors were used in this study. One rAAV vector, used in all of the control experiments, was constructed to express the EGFP gene under the control of a NSE promoter. Another rAAV vector was constructed to contain the rat µOR cDNA in place of the EGFP gene. A 6×His sequence was fused to the C terminus of the µOR gene so that the exogenously introduced µORs could be distinguished from the endogenously expressed µORs with an anti-His antibody. The titer of purified virus, determined by transgene expression in DRG cultures by using a serial dilution of the viral stock, was $4.2×10^8$ transducing units (t.u.)/ml for the NSE-EGFP virus (designated as rAAV-EGFP) and $2.6×10^8$ t.u./ml for the NSE-µOR virus (rAAV-µOR).

First investigated was µOR expression in cultured DRG neurons treated with rAAV-µOR. The mouse anti-His mAb was used to evaluate the expression of exogenous µORs; the rabbit polyclonal anti-µOR antibody was used to probe the expression of all, i.e., both endogenous and exogenous, µORs. In untreated cultured DRG neurons, none of the neurons were His-positive. About 50.0±2.9% (n=3) of cells expressed µORs endogenously. Five to 7 days after adding crude rAAV-µOR, 60.0±1.7% (n=6) of DRG neurons were labeled with anti-His antibody and 81.0±3.6% of cells were labeled with anti-µOR antibody. His-labeled cells were also labeled with anti-µOR antibodies. The µOR fluorescence in doubled-labeled neurons was usually much brighter than that in single-labeled neurons. Their cell processes were often labeled intensely. When purified rAAV-µOR was used, >90% of cultured DRG neurons became His-positive.

To infect DRG neurons with rAAV-µOR in vivo, a purified viral stock of rAAV-µOR was injected into the L4 and L5 ganglia (2 µl each). The rats showed no signs of paresis or other abnormalities afterward. The injected DRGs, stained with hematoxylin/eosin, retained their structural integrity; leukocytes were not present in the ganglia. The immune responses due to rAAV-µOR infection were therefore minimal. Studies of three animals in each rat group, 37.3% of neurons in the injected DRGs were brightly labeled with rabbit polyclonal anti-His antibody 3 weeks after the injection. A majority (about 25%) of them were small (diameter (d)<25 µm) and medium (25<d<35 µm) neurons, which likely mediate nociception. All His-positive neurons were also NeuN-positive, confirming the neuron specificity of the NSE promoter. The expression remained stable for at least 6 months. No His-labeled cells were found in the DRGs contralateral to the injected side. In injected DRGs, anti-µOR antibody labels were found in 76.3% of cells, a percentage significantly higher than the 50.1% of labeled neurons on the contralateral side. The increase in percentages of neurons expressing µORs suggests that the rAAV-µOR viron indeed infects neurons, many of which do not express or minimally express µORs endogenously. His labels in the spinal cord were also examined. His label was seen in axons and presumed nerve terminals in the dorsal column and laminae I-V of the spinal cord ipsi-, but not contralateral, to the injection; no spinal neuron cell bodies were labeled.

The type of DRG neurons, i.e., nociceptive and nonnociceptive neurons, infected by rAAV was also investigated. With some exceptions, it is generally believed that large (d>35 µm) and myelinated neurons mediate nonnociceptive sensations and small (d<=25 µm) and medium (25<d<=35 µm) unmyelinated or myelinated neurons mediate nociception (9). Neuronal types were therefore categorized according to their sizes and myelination. Almost all DRG neurons in the culture were His-labeled, suggesting that rAAV infected both nociceptive and nonnociceptive neurons. However, µOR expression in nonnociceptive neurons in vitro was difficult to assess quantitatively because large DRG neurons did not survive as well as small and medium neurons in cultures. The µOR expression was therefore quantified in vivo. Because mouse monoclonal His-antibody could not optimally label μORs in vivo, rabbit polyclonal His-antibody had to be used, which prevented double-labeling μORs in vivo with anti-His and anti-μOR antibodies. Different strategies were used. First, the percentages of neurons labeled with the anti-μOR antibody in the DRGs ipsi- and contralateral to the rAAV injection were determined. The results are presented in Table 1.

TABLE 1

DRG neuronal types infected by rAAV-_OR

|  | Small Cell d < 25 μm$^a$ | Medium Cell 25 < d < 35 μm | Large Cell d > 35 μm | Total$^b$ |
|---|---|---|---|---|
| μOR labeled$^c$ | | | | |
| Contralateral | 26.2 ± 2.8 | 19.8 ± 1.7 | 4.1 ± 0.3 | 50.1 |
| Ipsilateral | 33.0 ± 2.5 | 29.2 ± 2.2 | 14.1 ± 0.4 | 76.3 |
| Increase$^4$ | 6.8 | 9.4 | 10.0 | 26.2 |
| Double-labeled$^5$ | | | | |
| His + N52 | 2.2 ± 0.02 | 9.8 ± 0.08 | 12.2 ± 0.3 | 24.2 |
| His + peripherin | 5.1 ± 0.03 | 8.0 ± 0.1 | 0 | 13.1 |
| Sum$^6$ | 7.3 | 17.8 | 12.2 | 37.3 |

Total number of cells counted was set at 100%. All values stated are in percent.
$^1$d = cell diameter;
$^2$Total = total percentage of labeled cells, including small-, medium-, and large-sized cells;
$^3$Cells labeled with anti-μOR antibody;
$^4$Cells double-labeled with anti-His and anti-His or anti-His and antiperipherin antibodies.
$^5$Sum = sum of the percentages of double-labeled cells.

Higher percentage of neurons expressing μORs were found in ipsilateral DRGs. The increase in percentages of neurons expressing μORs (i.e., small cell, 6.8%; medium cells, 9.4%; large cell, 10.0%) suggests that the rAAV-μOR viron indeed infects neurons, many of which do not express μORs endogenously. Next, the DRGs were double-labeled with rabbit anti-His antibody and mouse anti-N52, which labels myelinated DRGs (10), or mouse antiperipherin, which labeled unmyelinated DRGs (11). About 7.3% of small cells, 17.8% of medium cells, and 12.2% of large cells were His-labeled, as shown in Table 1). These percentages were larger than the percentage increases examined with the anti-μOR antibody. These results suggest that rAAVs also infect neurons, especially medium-sized, that express μORs endogenously. Furthermore, two-thirds (i.e., (7.3±17.8)/37.3=0.67) of exogenous μORs were expressed in small and medium neurons, which likely mediate nociception. A third of exogenous μORs were expressed in large, presumably nonnociceptive, cells.

Figure 1B:
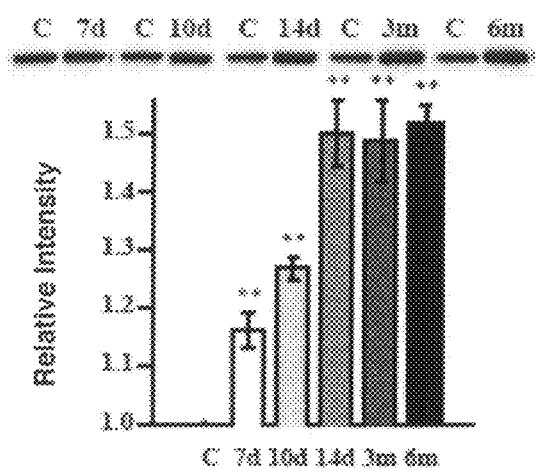
Figure 1C:
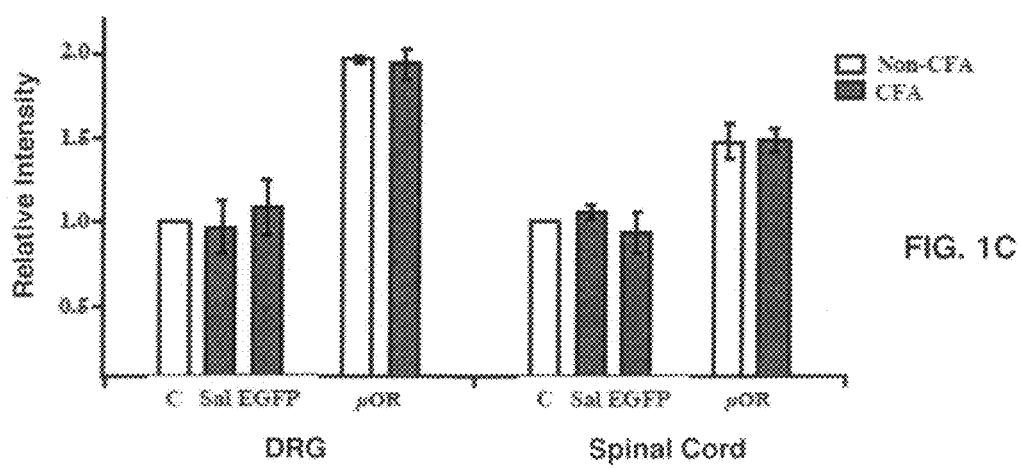
FIG. 1C is a bar graph showing μOR expression after inflammation. CFA was injected in the left paw of rats 3-4 weeks after rAAV infection. Ten days after CFA injection, DRGs and the spinal cord were removed. The μOR expression in inflamed rats injected with normal saline (N.S.) or rAAV-EGFP (EGFP) was not significantly different from the contralateral controls. The μOR expression in the ipsilateral DRGs or spinal cord of rAAV-μOR rats was significantly higher than the contralateral controls. Inflammation did not change the μOR expression.

The rAAV-derived increase in μOR expression was further quantified by Western blot analyses. The injected and contralateral ganglia were removed from the animals at different time points and probed with the anti-μOR antibody. Compared with the contralateral ganglia, μOR expression in the injected DRGs increased with time, plateaued at about 2-fold 14 days after the injection (FIG. 1A). The delay in reaching the plateau is likely caused by the time for the AAV, which is a single-stranded replication-defective DNA virus, to convert from single- to doubled-stranded DNA. Once it reached a plateau, μOR expression remained stable up to 6 months (the longest time point tested; FIG. 1A). The μOR expression in the spinal-cord segments innervated by the L4 and L5 ganglia was increased with a similar time course and reached a maximum increase of 1.5-fold (FIG. 1B). μOR expression in the DRG and spinal cord before and after inflammation was compared by using Western analyses. The results are presented in FIG. 1C. The relative blot intensity, i.e., μOR expression, in the DRG and spinal cord of normal saline and rAAV-EGFP rats after inflammation were not significantly different from their contralateral controls. The μOR expression of rAAV-μOR rats was considerably higher than the contralateral control (DRG: non-CFA=1.96±0.02, CFA=1.94±0.07; spinal cord: non-CFA=1.48±0.10, CFA=1.49±0.07). However, inflammation did not significantly alter μOR expression.

Enhanced Antinociceptive Effects of Morphine in rAAV-μOR Rats

To determine the functional consequence of the enhanced expression of μORs, the effects of morphine on thermal nociceptive responses (which are mediated by small and medium DRG neurons) in rAAV-injected rats were studied. The left L4-L5 ganglia of rats were injected with either the rAAV-EGFP or rAAV-μOR. Three to four weeks later, paw withdrawal latencies to noxious radiant heat were measured from the hind paw ipsilateral to the rAAV injection. The basal paw withdrawal latencies for rats infected with rAAV-μOR and rAAV-EGFP were indistinguishable (PWL=10.08±0.45 s, n=34 for rAAV-EGFP rats; PWL=10.29±0.46 s, n=36 for rAAV-μOR rats). In both rat groups, a s.c. morphine injection produced an increase in the paw withdrawal latencies, and the antinociceptive effect developed with a similar time course (FIG. 2A). However, the paw withdrawal latencies in rAAV-μOR rats were larger than those measured in rAAV-EGFP rats. To make sure that rAAV-EGFP itself did not produce unforeseeable behavioral consequences, morphine antinociceptive effects on the paw contralateral to the rAAV-μOR injection (n=6) and the paw in rats with saline injected in their DRGs (n=7) were studied. The behavioral responses in these two control groups were similar to the rats treated with rAAV-EGFP (FIG. 2A). Most control experiments hereafter were done with rAAV-EGFP rats.

Figure 3A:
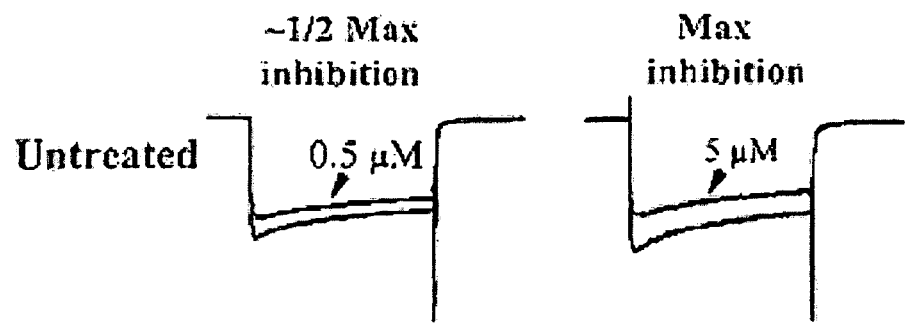
FIGS. 3A-3C are graphs showing the inhibitory effects of DAMGO on $Ca^{2+}$ channels in isolated DRG neurons infected with rAAV-μOR. $Ba^{2+}$ currents were recorded before and after DAMGO treatment in untreated (FIG. 3A) and rAAV-μOR-infected (FIG. 3B) DRG cells. The DAMGO doses for about half-maximal and maximal inhibition are indicated. DAMGO induced larger maximal inhibition and produced about half-maximal inhibition at a lower dose in rAAV-μOR cells. Membrane potentials were held at −60 mV.
Figure 3B:
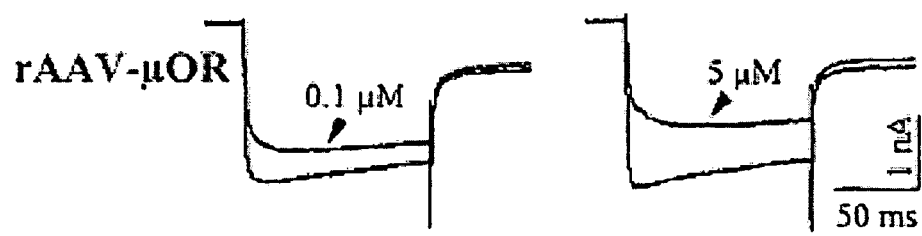

The enhanced effect of morphine in rAAV-μOR rats was observed consistently at different morphine doses. Therefore, the morphine dose-response, expressed as the MPE, for rAAV-μOR rats was shifted to the left of that for rAAV-EGFP rats (FIG. 3B). The morphine dose to produce 50% MPE, i.e., A50, was 2.34 mg (95% confidence limits, 1.78-2.88 mg) for rAAV-μOR rats and was 3.63 mg (2.95-4.27 mg) for rAAV-EGFP. The increased antinociceptive effects of morphine persisted in rAAV-μOR rats for at least 3 months (the longest period tested). The morphine effects on thermal nociceptive responses in rAAV-EGFP and rAAV-μOR rats with inflammation were also studied. CFA was injected into the hind paw and nociceptive responses were examined 5-14 days later. Compared with non-CFA-treated rats, the basal paw withdrawal latencies to heat were considerably reduced (PWL=6.02±0.35 s, n=12 for rAAV-EGFP rats; PWL=5.92±0.33 s, n=19 for rAAV-μOR rats). Morphine treatment increased the paw withdrawal latencies in both rAAV-EGFP and rAAV-μOR rat groups (FIG. 2C). The nociceptive effects of morphine in rAAV-μOR rats were again larger than those in rAAV-EGFP rats. The extent of increase in paw withdrawal latencies induced by rAAV-μOR treatment was more pronounced in CFA rats (FIG. 2C) than in non-CFA rats FIG. 2A). This finding could also be seen in morphine dose-response curves (FIG. 2D). The increase in the MPEs of rAAV-μOR rats, especially for morphine doses ≥4 mg/kg, was larger after CFA treatment. The A50 for rAAV-μOR rats was 2.63-fold lower than that for rAAV-EGFP rats (rAAV-μOR, A50=3.02 mg (2.75-3.31 mg); rAAV-EGFP, A50=7.94 mg (6.6-9.3 mg)). Thus, enhanced μOR expression increases the efficacy of morphine; the increase is further potentiated after inflammation. Comparing the morphine dose-response curves of non-CFA and CFA-treated rAAV-EGFP rats, the dose-response curve of CFA-treated rAAV-EGFP rats was shifted to the right (non-CFA, A50=3.64 mg; CFA, A50=7.94 mg) (FIGS. 2B and 2D). That is, more opiates are required to overcome the enhanced nociception caused by inflammation. In contrast, the shift in morphine dose-response curve in rAAV-µOR rats before and after inflammation (non-CFA, A50=2.34 mg; CFA, A50=3.02 mg) was not statistically significant, a result of the much more pronounced enhancement of antinociceptive effect of morphine in rAAV-µOR rats after inflammation.

Enhanced Block of $Ca^{2+}$ Channels in rAAV-µOR-Infected Neurons

Figure 3C:
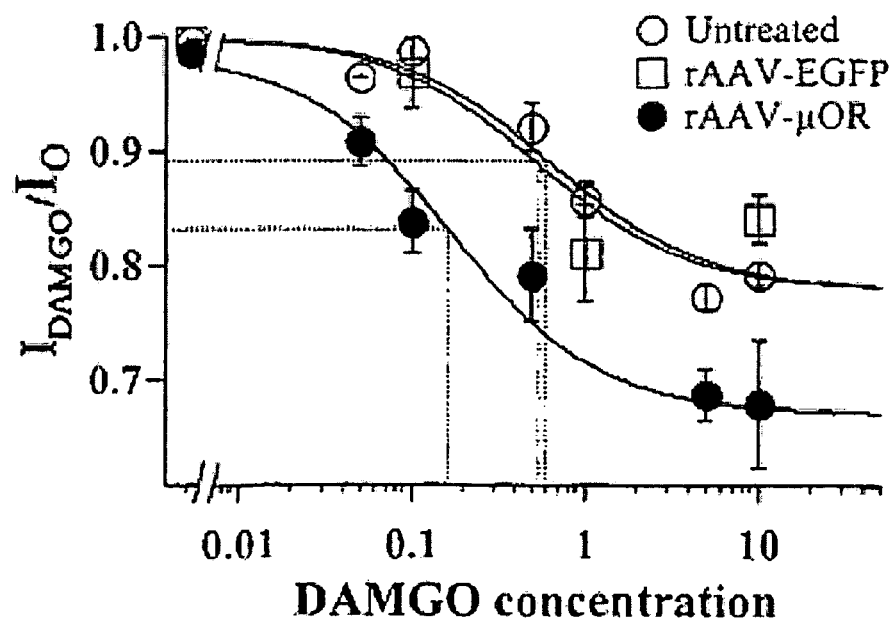

It is well established that µ-opioids inhibit high-threshold voltage-dependent $Ca^{2+}$ currents in DRG neurons. To determine whether the enhanced µOR expression alters opioid inhibition of $Ca^{2+}$ currents, the effects of the µ-opioid agonist, DAMGO, on the activity of high-threshold $Ca^{2+}$ channels in untreated, rAAV-EGFP-treated, and rAAV-µOR-treated cultured DRG neurons were compared. rAAV virons were added to neurons 1-2 days after plating. Seven days after the infection, perforated patch whole-cell recordings were performed on the cells. External $Ca^{2+}$ was replaced by $Ba^{2+}$ to avoid rapid rundown of current responses. DAMGO was found to block $Ba^{2+}$ currents in small and medium DRG cells (diameter, 18-35 µm). The block was observed for both control (untreated and rAAV-EGFP-treated) and rAAV-µOR-treated DRG neurons (FIGS. 3A-4C). However, a larger percentage of cells responded to DAMGO inhibition in the rAAV-_OR group (89.2%, n=34) than that in the control groups (untreated cells, 57.1%, n=14; rAAV-EGFP, 54.5%, n=11). In addition, the maximal block of $Ba^{2+}$ currents in rAAV-µOR cells was significantly higher (FIGS. 3A and 3B). The slowing of activation of the currents in rAAV-µOR neurons became more evident. The DAMGO dose required for about half-maximal inhibition in rAAV-µOR cells was severalfold lower than that in the control groups (FIG. 3C). When the dose-response curves of the DAMGO block were fit with the Hill equation, the maximal block was about 22.02±0.01% for untreated cells, 22.02±0.01% for rAAV-EGFP cells, and 31.63±0.03% for rAAV-µOR cells. The apparent affinity for DAMGO inhibition ($IC_{50}$) was 0.53±0.03 µM for the rAAV-EGFP and 0.64±0.19 for the untreated cells. The $IC_{50}$ was 0.17±0.06 µM for the rAAV-µOR cells, a 3.1- or 3.8-fold increase in the affinity. Therefore, the potency and efficacy of opioid inhibition are significantly increased after rAAV-µOR infection.

Example 3

Studies into the Efficiencies of Transgene Expression

Preparation of rAAV Plasmid Constructs and Viral Stocks rAAV plasmid constructs and viral stocks were prepared as described in Example 1. The titer of purified rAAV-µOR used in this experiment was $2.6 \times 10^8$ transducing units (t.u.)/ml.

Transduction of Cultured DRG Neurons

DRGs were taken from 13 to 16 day-old rats and desheathed in Hanks's balanced salt solution (HBSS). DRGs were digested in Earle's balanced salt solution (EBSS) with 1 mg/ml trypsin and 1 mg/ml collagenase at 35° C. After one hour, additional culture medium was added to stop enzymatic reaction. The cells were pelleted by centrifugation at 50×g for 6 minutes. The pellet was resuspended in Eagle minimum essential medium (MEM, Life Technologies) and plated on coverslips in a 24-well culture plate. D R G cells were cultured in $1.2 \times 10^4$ cells/well. The cells were incubated at 37° C. with 5% $CO_2$. Twenty-four to forty-eight hrs after plating, DRG cells were transduced with the virus. The viral stock was serially diluted in OptiMEM (Life Technologies). Following 1.5 hr incubation at 37° C., MEM containing 20% of FBS was added to reach the final concentration of 10% FBS and incubated overnight. Medium was replace by 10% FBS, medium the next day. Transduction efficiency was checked 10-14 days treatment.

Microinjection to the Hindfoot, Sciatic Nerve, and the DRG

For subcutaneous injection, 1 week or 3 weeks old rats (male Sprague-Dawley) were used. 10 µl of viral solution was injected subcutaneously into the ventral and dorsal skin of the hindfoot. Animals were sacrificed 1, 3, or 6 weeks later. Transduction efficiencies in DRGs were assessed.

For nerve injection, 25-30 days old rats were anaesthetized with a pentobarbital sodium solution (i.p., 50 mg/kg). The sciatic nerve was surgically exposed. 2 µl of viral solution was delivered slowly (20 min) into the nerve through a glass micropipette connected to a Hamilton syringe. The pipette was pulled out after a 10 min wait. For DRG injection, 25-30 days old rats were anaesthetized as described above. The left L4 and L5 DRGs were exposed by removing part of the vertebrates. Viral solution (2 µl) was delivered to each DRG using the same procedure as described for the nerve injection.

Intrathecal Microinjection to the Spinal Cord

For intrathecal injection, 25-30 days old rats were used. The left lumbar spinal cord was exposed by partial laminectomy. 5 µl viral solution was infused into the left side of the subarachnoid space at the lumbar enlargement of the spinal cord using a glass micropipette as described. Injection usually took 10 minutes, and the pipette was pulled out after a 10 min wait.

Histology

Cultured DRG cells on coverslips were fixed with 4 paraformaldehyde in 0.1 M phosphate buffer for 1 hr at 4° C. Animals were anesthetized with a pentobarbital sodium solution (i.p., 50 mg/kg) and perfused by cardiac puncture with normal saline and followed by 4 paraformaldehyde in 0.1 M sodium phosphate buffer (pH 7.4). Dorsal root ganglia (L4-L6) and the lumbar spinal cord were dissected and incubated in the same fixative solution for 2 hr at 4° C. The tissue was then transferred to a 30% sucrose solution and stored at 4° C. overnight. For sectioning, the tissue pieces were put in the OTC embedding medium and placed on a cryostat stage. DRG tissue sections (10 µm thick) or spinal cord sections (16 µm thick) were serially collected. To visualize EGFP fluorescence directly, cells or tissue sections were rinsed with PBS for 5 min, coverslipped with the No-Fade mounting solution (Vector), and viewed under a fluorescence or a confocal microscope. Untreated cultured DRG neurons, DRGs, and the spinal cord were used as controls. In some experiments, rabbit anti-GFP (Chemicon, 1:200) was used to label EGFP; Cy3-conjugated IgG (Jackson ImmunoReseach, 1:400) was the secondary antibody. Mouse anti-NeuN (Chemicon, 1:200) was used to label neurons. Alex Fluor 546 goat anti-mouse IgG (Molecular Probes, 1:200) was used for visualization.

Cell Counting

To determine the percentage of rAAV transduced DRG neurons in vitro, EGFP-negative and positive cultured cells on coverslips were counted under a fluorescent microscope. Three coverslips were used for each viral solution. For in vivo studies, EGFP labels were visualized directly on tissue sections (10 µm thick) without further processing. To minimize the possibility of double counting, cells were counted by using stereological-counting techniques. The percentages of EGFP labeled cells from three animals in each delivery method were averaged.

Induction of Inflammation

Three to four weeks after infection of rAAV, 100 μl complete Freund's adjuvant (CFA) (*Mycobacterium butyricum*; DIFCO, Detroit, Mich.) emulsion (1:1 peanut oil/saline, 10 mg *Mycobacterium*/ml) was injected into the plantar surface of the rat left hindpaw to induce inflammation. Behavioral experiments were performed 5-14 days following the CFA injection.

Behavioral Tests

Thermal hyperalgesia to radiant heat was assessed using the method described in Hargreaves. Prior to behavioral experiments, rats were acclimated in plexiglass boxes placed on a platform for 30 min/day for 5 days. Paw withdrawal latencies were obtained by placing a radiant heat source under the plantar surface of the hindpaw and recording the time elapsed from the onset of radiant heat stimulation to the withdrawal of the paw. The heat intensity was adjusted to give a baseline latency of ~5 sec in CFA rats. A cut-off time of 30 sec was set to prevent possible tissue damage. To obtain baseline paw withdrawal latencies, three measurements separated by a 5-min interval were made for the rat's hindpaw and scores were averaged. The antinociceptive effects of morphine were evaluated by measuring paw withdrawal latencies before and every 10-min after the subcutaneous morphine administration. Morphine antinociceptive responses were expressed as maximum possible effect (MPE) using the relation MPE=(postdrug PWL−predrug PWL)/(cut-off PWL−predrug PWL)×100.

Example 4

Studies into the Efficiencies of Transgene Expression

Efficient Transduction of DRG Neurons In Vitro

Cultured DRG neurons 24-48 hr after plating were treated with the virons of rAAV-EGFP under the control of the NSE promoter. Two different viral dosages ($2.3 \times 10^4$ or $2.3 \times 10^3$ transducing unit/well) were used. A few EGFP expressing neurons began to appear 3-4 days postinfection. However, the fluorescence was limited in the cell body, and its intensity was low. EGFP expression increased with time. By 7 days, neurons became brightly green, and fluorescence was seen in proximal and distal processes. At 14 days postinfection, the EGFP expression remained high. The percentage of EGFP-positive neurons at the high viral dosage (i.e., at $2.3 \times 10$ transducing unit/well) was much higher (97±2.3, n=4), than that at the low viral dosage (21±1.7, n=4). The time course and intensity of EGFP expression in cultures treated with different dilutions of the viral solution were indistinguishable. Intensive EGFP fluorescence persisted until the end of the culture (about 3 weeks). Schwann cells, characterized by their spindle biopolar shape and fusiform muclei, were not labeled.

A Few DRG Neurons Transduced by Subcutaneous Injection of rAAV in the Hindfoot

To determine the best route of gene delivery, transduction of DRG neurons by injecting rAAV-EGFP in the rat hindfoot was attempted. A 10 μl viral stock ($4.2 \times 10^8$ transducing unit/ml) was injected subcutaneously into either dorsal or ventral surface of the hindfoot of 3 weeks old rats. No EGFP-positive cells were found in the DRGs at 3 or 6 weeks postinjection. When rAAV-EGFP was injected into the dorsal surface of the hindfoot of 1-week old rats, no labeled cells were observed either. However, when viral solution was injected into the ventral surface of the hindfoot of 1-week old rats, one to two EGFP-labeled cells were observed in ipsilateral L4-6 DRGs at 3 weeks postinjection (n=2), although no labeled cells were found at 1 week postinjection (n=1). The number of EGFP-positive cells, stained with the anti-GFP antibody, did not increase further when DRGs were examined at 6 weeks postinjection (n=2). No glial cells were transduced.

Efficient Transduction of DRG Neurons with Injection of rAAV in the Sciatic Nerve.

Figure 4:
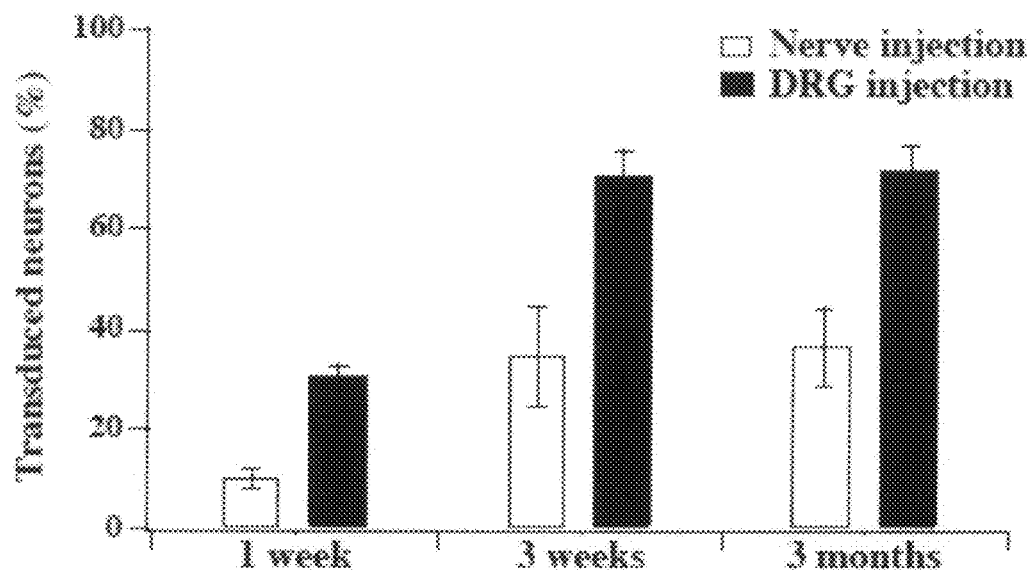
FIG. 4 is a bar graph showing the efficiencies of EGFP expression following direct DRG or nerve injection. The percentages of neurons transduced by rAAV-EGFP were 10.3±1.8 (n=3), 34.8±9.9 (n=3), and 36.0±7.5 (n=5) 1 week, 3 weeks, and 3 months after sciatic nerve injection. The percentages of neurons transduced were 29.4±2.9 (n=3), 69.6±5.7 (n=3) and 70.6±5.7 (n=3) 1 week, 3 weeks, and 3 months following direct DRG injection.
Figure 5A:
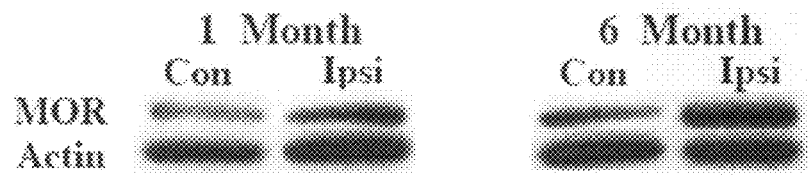
FIG. 5A is an image of Western blots of EGFP expression in L4-6 DRGs 1 and 6 months after injection of viral solution into the nerves. DRGs without any viral injection were used as controls (CON).
Figure 5B:
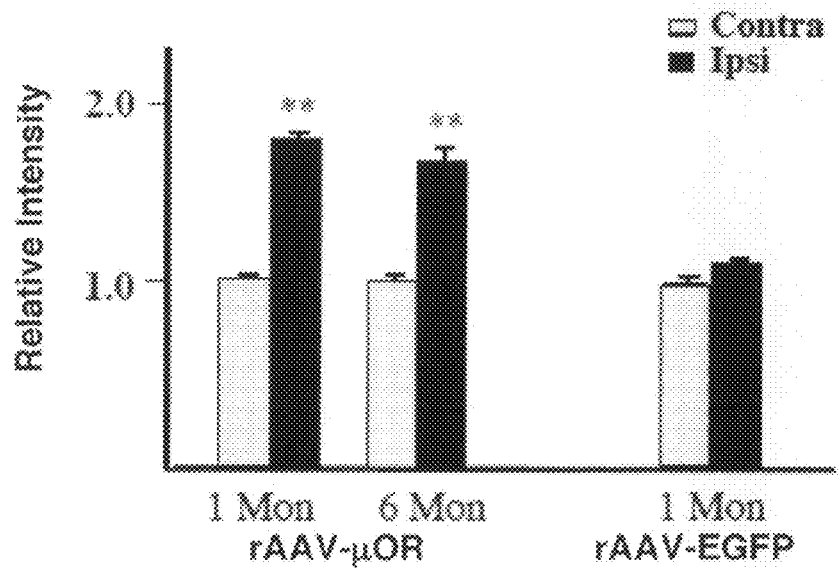
FIG. 5B is a bar graph showing the average relative intensities of protein bands (n=6). The intensity obtained from control DRGs was set to 1.

Transduction of DRGs following injection of rAAV-EGFP (2 μl) into the sciatic nerves of 21-25 days old rats was studied. As shown in FIG. 4, at 1 week postinjection, 10.3±1.8 (n=3) of DRG neurons were weakly labeled, and, at 3 weeks, 34.8±9.9 of neurons were labeled (n=5). The labeled cells showed intensive fluorescence, and EGFP expression became visible in dorsal roots and the spinal dorsal horn (n=4). NSE driven EGFP was selective for neurons because satellite cells were not labeled. No fluorescence was seen in DRG neurons of uninjected rats. EGFP expression plateaued after 3 weeks; 36.0±7.5 (n=5) of neurons in DRGs were transduced at three months, as shown in FIG. 4. Western analyses of EGFP expression indicated that the EGFP expression reached its peak value at one month postinfection and persisted for at least six months (FIGS. 5A and 5B).

Strong Neuronal Transduction Following Direct Injection of rAAV into the DRG.

Experiments were then conducted to examine EFGP expression after injecting 2/μl ($8.4 \times 10^5$ transducing units) of rAAV-EGFP directly into L4-5 DRGs of 21-25 days old rats. At 1 week postinjection, 29.4±2.9 (n=3) of neurons were labeled (FIG. 4). Fluorescence was observed in cell bodies and axons near the ganglion. Dorsal roots innervating the dorsal horn of the lumbar cord were also labeled. At 3 weeks, the percentage of cells expressing EGFP greatly increased. On average, 69.6±5.7 (n=3) of neurons in the ganglia were labeled (FIG. 4). All EGFP-labeled were Neu-N positive, indicating the neuron-specific expression. At 3 months postinjection, 70.6±5.7 (n=3) of DRG neurons were labeled (FIGS. 5A and 5B). Intensive EGFP fluorescence was detected in a large number of nerve fibers innervating both the dorsal and anterior horns of the spinal cord ipsilateral to the injection. No cell bodies of spinal cord neurons were labeled, suggesting that rAAV-EGFP was not transported across central terminal synapses. Bright fluorescent labels were also seen in the sciatic nerve fibers. To determine the length of expression of rAAV, EGFP labels were examined at 8 and 12 months postinjection. At 8 months, DRG neurons stayed brightly fluorescent but sciatic nerves and nerve fibers in the spinal cord (n=3) were not as bright as that at 3 months. At 12 months, the EGFP expression in neurons and the sciatic nerves postinjection were somewhat reduced (n=3). Peripheral tissue in the hindfoot ipsilateral to the injected DRGs was also inspected. Labeled nerve fibers were found around muscle cells, blood vessels, and the subcutaneous tissue. No labeled nerve fibers were found in uninjected Animals.

Intrathecal Delivery of rAAV-EGFP Results in EGFP Expression in the Dorsal Horn

To determine whether rAAV viral vectors can be efficiently delivered to the spinal cord, viral solution (5 μl) was injected into the subarachnoid space on the lateral side of the lumbar enlargement of the spinal cord of 25-30 days old rats. EGFP labeled neurons started to appear in the dorsal horn at 1 week postinjection (n=1). Fluorescent spinal neurons nearly doubled at 3 weeks. Most of them were located in the laminae I and II of the dorsal horn (n=2). Some were in laminae III and IV. The caudal-rostral spread of the EGFP expression was examined. Labeled cells were found in spinal cord sections up to 2 mm away from either side of the injection site; EGFP labeled fibers could be seen up to 6 mm away from the injection site. The lateral spread of viral solution was limited because EGFP-positive neurons were not found on the contralateral side of the spinal cord. To ascertain that the labeled cells were neurons, the spinal cord sections were doubled labeled with the anti-NeuN antibody. All EGFP labeled cells were found to be NeuN positive, indicating again that the NSE promoter selectively drove EGFP expression in neurons. Since none of the L4-L6 DRGs on either side of the spinal cord were labeled, the virions did not appear to retrogradely cross spinal cord-afferent synapses.

Transduction of μOR Genes into DRGs Enhances Morphine Analgesia

Figures 6A, 6B:
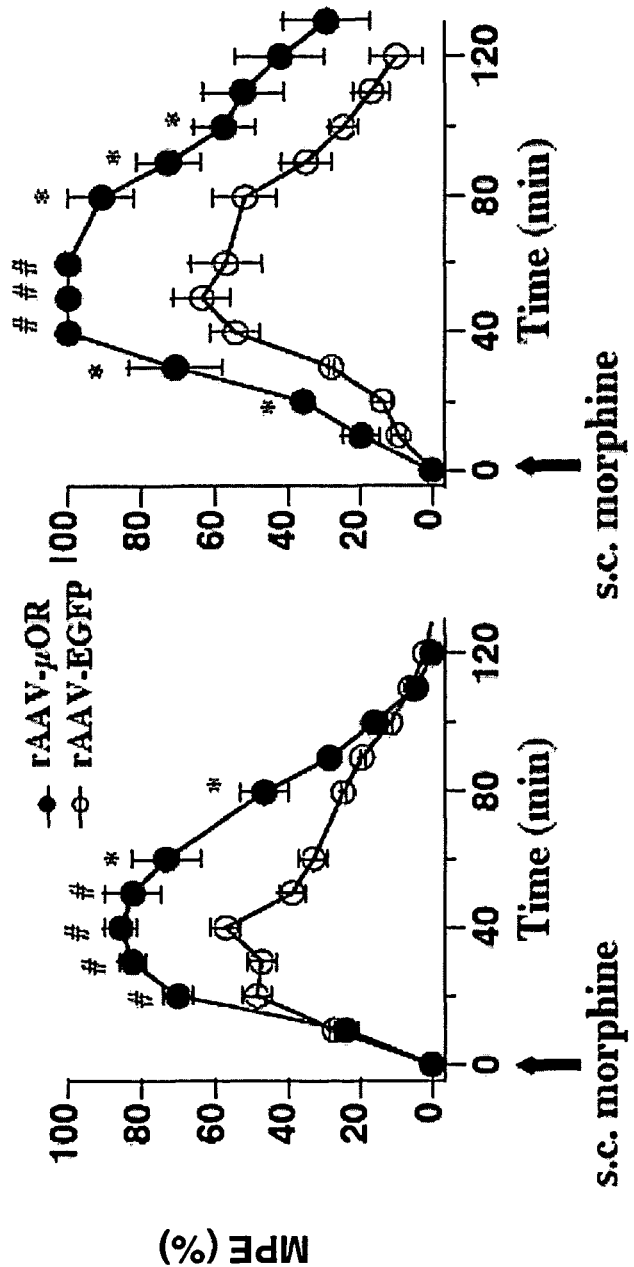
FIGS. 6A and 6B are graphs showing that morphine antinociceptive effects are enhanced in inflamed rats injected with rAAV-μOR.

To determine if the gene transfer strategy can be used in treatment of nociception, μOR expression in DRGs was increased by delivering rAAV-μOR into DRGs and changes in morphine analgesia were studied. The two most effective routes of gene delivery, i.e., direct DRG and sciatic nerve injection of rAAV-μOR, were used to deliver the μOR gene. The antinociceptive effects of morphine for inflammatory pain were examined. rAAV-μOR or rAAV-μOR EGFP were injected (as controls) into the left L4-L5 DRGs (FIG. 6A) or into the left sciatic nerve (FIG. 6B). Three to four weeks later, paw inflammation was induced by an injection of complete Freund's adjuvant (CFA) into the plantar surface of the left hindpaw. Within 12 hr of CFA treatment, the paw showed signs of inflammation, i.e., edema and redness, which lasted for more than 2-3 weeks. Five to fourteen days after CFA treatment, behavioral tests, i.e., paw withdrawal latencies (PWLs) or maximum possible effects (MPEs) in response to a radiant heat source placed under the hindpaw, were used to study the effect of morphine analgesia. In the rat group injected with rAAV into DRGs directly (FIG. 6A), the MPEs in the EGFP rat group increased (i.e., analgesia) following subcutaneous injection of morphine. The MPEs peaked at 30-40 min and dissipated within 100-120 min of morphine treatment (FIG. 6A). In the μOR rat group, the morphine analgesic effect developed with a similar time course. However, the MPEs were significantly larger, clearly indicating an increase in morphine analgesia. Injection of rAAV-μOR into the sciatic nerve also resulted in similar enhancing morphine antinociceptive effects (FIG. 6B). The enhancement persisted for three months after the injection of rAAV-μOR.

Example 5

Upregulation of μ-Opioid Receptors in DRG by Remote Nerve Injection rAAV-μOR or rAAV-EGFP was injected into the sciatic nerves of 1 month old, male Sprague-Dawley rats. Briefly, rats were anaesthetized with pentobarbital sodium solution (50 mg/kg, i.p.). A 1.5 cm incision was made in the dorsal surface of the upper thigh and underlying muscle. The sciatic nerve was exposed using blunt dissection. A very thin needle made by glass was inserted into the thecal of the sciatic nerve. A 2-μl viral solution was injected. The skin incision was closed with wound clips. The rat recovered hours later.

After four weeks of injecting rAAV-μOR or rAAV-EGFP into the thecal of sciatic nerve, the rats were anaesthetized with pentobarbital sodium solution (50 mg/kg) and perfused with the fix solution (4% paraformaldehyde and 0.2% picric acid in PBS) at 40° C. DRGs were removed and postfixed in the same solution for another 2-4 hours. The tissues were then put into 30% sucrose solution overnight and cut by cryostat into 10 μm sections. A polyclonal rabbit anti-His antibody (Santa Cruz Biotechnology, 1:200) was used to detect the transduced μORs. Visualization of His-peptide was achieved by using fluorescein anti-rabbit antibody (Vector).

Total proteins were extract from DRGs of sciatic nerve injected rats using standard methods. A polyclonal rabbit anti-μOR antibody (DiaSorin, 1:1000) was used as the primary antibody to identify both endogenous and transduced μORs. Blots were detected by using secondary antiserum coupled to horseradish peroxides and developed by using the enhanced chemiluminescence kit (Amersham). Actin, used as an internal control, was labeled with mouse anti-Actin antibody (Chemicon, 1:1000). The data were analyzed by using the LYNX 5000 image analyzer.

After four weeks of injecting viral vector to the sciatic nerve, a catheter was placed in the intrathecal space to the lumbosacral level of the spinal cord for the intraspinal administration of morphine. Complete Freund Adjuvant (CFA, *mycobacterium tuberculosis*, suspended in an oil/saline 1:1 emulsion, 1 mg *mycobacterium*/ml) was then injected into the left paw to induce inflammation. After five days of CFA administration, thermal hyperalgesia to radiant heat was assessed by using a paw-withdrawal (PWLs) test. To measure PWLs, a radiant heat source from a projection bulb was placed below the mash net directly under the plantar surface of the hindpaw. The heat intensity was adjusted to give a baseline latency of about 15 Sec. The cut-off time of 30 sec was preset to prevent possible tissue damage. The baseline of paw withdrawal latencies was obtained by averaging three measurements separated by a 10-min interval. Morphine (morphine sulfate) was dissolved in saline and intrathecally injected into the rats. The morphine effect was determined from the measuring paw withdrawal latencies before and after morphine administration. Data were expressed as maximum percent effect (MPE), as discussed above.

All data were expressed as mean±S.E.M. Student's test was used to assess the significance of changes between two means. A $P<0.05$ was considered significant. Changes before and after morphine treatment within one rat group were analyzed with the one-way ANOVA followed by post-hoc Newman-Keuls analysis. Dose-response curves were plotted as MPE vs dose and fitted with the logistic equation. The dose estimated to produce 50% MPE, A50, and 95% confidence intervals were determined.

The rAAV-μOR vector used in this study was constructed to contain the His-tagged μOR gene. The His tag allowed the exogenously expressed μORs to be distinguished from the endogenously expressed μORs by their labeling with the anti-His antibody. The rAAV-EGFP was used in the control experiments. Both viral vectors were under the control of the NSE promoter so that the target genes were selectively expressed in neurons. Following rAAV-μOR viral vectors (2 μl) injection into the thecal of sciatic nerves, rats groomed and ate normally and did not show signs of paresis. Three to four weeks after the nerve injection, L4 and L5 DRGs on both ipsilateral and counterlateral sides of the injection were removed and processed immunocytochemically with rabbit polyclonal anti-His antibody. His-labels were seen in 35% of DRG neurons ipsilateral to the side of injection, while no His labels were found in the DRGs countralateral to the injection. Most labeled cells are small (<25 μm) and medium (25-35 μm) in size. The expressions of μORs were studied 1, 3, and 6 months after the injection. The number of neurons labeled with His and the intensity of the labels were not substantially diminished up to 6 months. During this period, the integrity of cells remained intact, and no obvious immune responses resulting from the rAAV infection were observed.

To further quantify the upregulation of μORs, the receptor expression was probed with the anti-μOR antibody by Western analyses. Ipsilateral and counterlateral DRGs were extracted from rats at 1 and 6 months after the nerve injection.

The μOR expression in the ipsilateral DRGs was increased by 1.65±0.1-fold (n=3, P<0.01) at one month and by 1.60±0.2-fold (n=3, P<0.05) at 6 months. Thus, nerve injection of rAAV-μOR-His substantially enhanced μOR expression in DRGs, and the enhancement persisted for at least 6 months.

Basal nociceptive responses of these injected rats were determined by measuring the paw withdrawal latency to noxious radiant heat stimuli. Rats injected with rAAV-EGFP into the sciatic nerve were used as controls. The paw withdrawal latencies of rAAV-μOR rats was 13.8±0.4 sec (n=12), which was not significantly different from the paw withdrawal latencies of rAAV-EGFP rats (13.0±0.6 sec, n=12).

The basal nociceptive responses of rAAV-μOR and rAAV-EGFP rats with chronic inflammation were determined next. To induce inflammation, CFA was injected into the hindpaw of the rats that had been infected with rAAV-EGFP or rAAV-μOR four weeks before. Within twelve hours after the CFA injection, the hindpaws began to swell. The swelling usually lasted for ~14 days. The nociceptive responses to heat were tested 5-14 days following CFA injection. Compared with non-CFA rats, the basal PWLs of both rat groups after CFA treatment were considerably reduced (CFA rAAV-EGFP rats, 6.20±0.14, n=12; CFA rAAV-μOR rats, 6.48±0.09, n=12). Again there was no significant difference in the paw withdrawal latencies between EGFP and μOR rat groups.

Figures 7A, 7B:
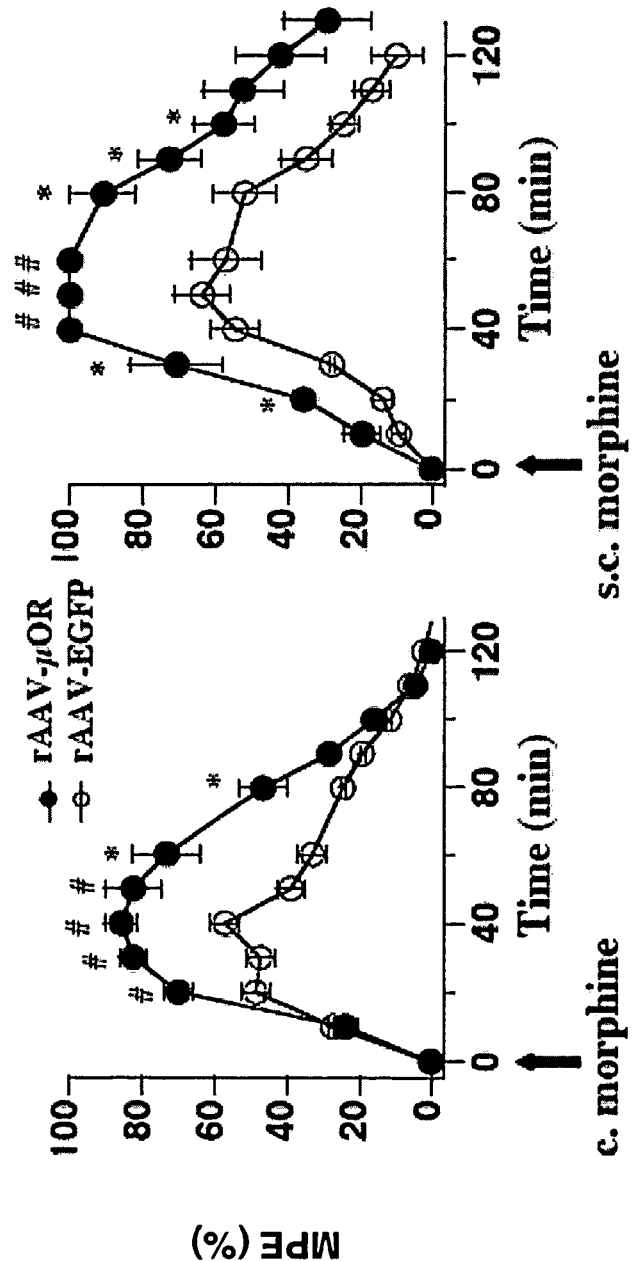
FIG. 7A is a graph showing the time courses of morphine effects following intrathecal (i.t.) administration of 1 μg morphine in rAAV-EGFP and in rAAV-μOR rats.
FIG. 7B is a dose response curve of morphine effects following intrathecal (i.t.) administration of 1 μg morphine in rAAV-EGFP and in rAAV-μOR rats.

The inflamed rats were than used as a chronic pain model to study the antinociceptive responses of morphine in rAAV-μOR rats. Morphine was administered intrathecally. Therefore, only μORs at the spinal level, including those at the central terminals of DRGs, were activated. The time courses of morphine effects following intrathecal (i.t.) administration of 1 μg morphine in rAAV-EGFP and in rAAV-μOR rats are shown in FIG. 7A. The maximum possible effect (MPE) in rAAV-EGFP peaked at 15-20 min, and the effect dissipated 50 min later. The time course of morphine effects in rAAV-μOR rats was similar to that in rAAV-EGFP rats. However, the MPE was 2.2 fold higher in rAAV-μOR rats than in rAAV-EGFP rats (FIG. 7A). This indicates that the efficacy of morphine was substantially increased following upregulation of μORs. Similar increases were also observed when 3 μg and 7 μg morphine were used (FIG. 7B). From the dose response curves, it was found that the dose of morphine producing 50% of MPE (A50) was 7.0 μg in rAAV-EGFP rats and was 1.2 μg in rAAV-μOR rats. There was a 5.8 fold increase in morphine efficacy in rAAV-μOR rats. These results suggest that nerve injection rAAV-μOR significantly enhances the expression of μORs and substantially increases the efficacy of intrathecal morphine.

Example 6

Upregulation μ-Opioid Receptors in Dorsal Root Ganglion Neurons Enhances Morphine Analgesia in Neuropathic Pain Rats Using a genetic approach to upregulate v-opioid receptors (μORs) in dorsal root ganglia (DRGs), it was determined whether this manipulation would improve morphine efficacy in the treatment of neuropathic pain.

To generate neuropathic pain in rats, the left common peroneal and the tibial nerves were transected while leaving the sural nerve intact. All rats developed a deformity in the left foot. The mechanical sensitivity of the lateral plantar paw surface, an area innervated by the sural nerve, were examined. Mechanical allodynia was determined by measuring the paw withdrawal threshold in response to von Frey filament stimulation. The force required to elicit paw withdrawal dropped precipitously from ~12 g before surgery to 1.85 g two days after surgery. The threshold dropped to less than 1 g seven days after surgery and maintained at this low level for at least two months. Thus, the spared nerve injury (SNI) rats showed signs of extreme mechanical allodynia for an extended period of time. This hypersensitivity was not observed in normal rats or in rats subjected to sham operation.

The antinociceptive effects of intrathecal morphine was then examined in SNI rats. Intrathecal injection of morphine (1-10 μg) was not effective in relieving mechanical allodynia in these rats. Compared with normal rats, the expression of μORs in small- and medium-sized DRG neurons in SNI rats was significantly reduced. There was no μOR expression in large-sized DRG neurons in injured rats, similar to that observed in normal rats. An adeno-associated viral (rAAV) vector containing μ opioid receptors (μORs) gene (rAAV-μORs) was introduced into DRGs through sciatic nerve injection. The expression of μORs in DRG neurons ipsilateral to the injection was increased in all sized neurons, including large DRG neurons, after 4 weeks. The antinociceptive effects of i.t. morphine was dramatically enhanced, as shown in FIGS. 8A and 8B. These results suggest that upregulation of μORs in DRG neurons would be an useful strategy for the treatment of neuropathic pain.

Example 7

Upregulation of δ-Opioid Receptors (dOR) in Nerve Injured Rats

To increase the transduction efficiency of rAAV-dOR, the AAV serotype, AAV1 or AAV5, in addition to AAV2, was used to construct the rAAV-dOR gene. In some experiments, the promoter CMV instead of the neuron-specific endolase promoter was used in the rAAV-dOR gene construct. dOR-FLAG DNA, instead of rAAV-dOR, was used some times to upregulate δ-opioid receptors expression in sensory neurons. Trigeminal ganglia (TGs), instead of DRGs, were also used in some experiments. Experiments were conducted in control or nerve injury in rats. Behavioral, immunocytochemical and Western analyses were used for the studies.

Similar method as described before was used to induce inflammation To produce the nerve-injury in the rat paw, spared nerve injury (SNI) in rats was generated by transecting the sural and common peroneal sciatic nerves in the left rat leg while leaving the tibal nerve intact. To induce inflammation in the trigeminal nerve innervated areas, rats were lightly anesthetized with pentobarbital. CFA (10-50 μl) was injected into the rat temporomandibular joint (TMJ) 3-4 weeks after infection of rAAV-dOR. Behavioral experiments were performed 5-14 days after the CFA injection. To induce spare nerve injury in the trigeminal nerve, the infraorbital nerve branch of the maxillary nerve was ligated and the ophthalmic and mandibular nerves were left intact.

δ-opioid receptor expression was enhanced in dorsal root ganglia (DRGs) by injecting rAAV-dOR into the ganglion or into the sciatic nerve or by injecting dOR-FLAG DNA intrathecally. The δ-OR receptor expression was enhanced in the trigeminal ganglon by injecting rAAV-dOR into the trigeminal ganglion or into the maxillary nerve.

Three to four weeks later, the effects of morphine or other analgesic drugs on mechanical allodynia in SNI rats were determined behaviorally. Rat hindpaw withdrawal (PW) thresholds in response to stimulation of Von Frey filaments were measured. Each test consisted of applications of a series of von Frey filaments (ranging from 0.4 to 15.0 g) to the lateral plantar surface of the tested paw until it withdrew or for a maximum of 60 s. To avoid injury during tests, the cutoff strength of the von Frey filament was 15 g. The up and down method described by Chaplan et al. (12) was used to determine the PW threshold. Mechanical threshold or the maximum possible effect (MPE), i.e., ((test−min)/(max−min)]× 100%, was used to calculate morphine mechanical analgesic effects.

Spontaneous nociceptive and evoked mechanical allodynic behavioral responses to trigeminal nerve innervated facial areas were assessed. Spontaneous nociceptive responses were determined by counting the number of face groomings in the ipsilateral infraobital nerve territory (for nerve-ligated rats) or in the lateral surface of the ipsilateral TMJ (for CFA rats) over a 5-min period. Evoked thermal hyperalgesic responses will be determined by measuring head withdrawal latencies in response to radiant heat produced by a lamp aimed at the lateral surface of the TMJ for CFA rats or at the vibrissal pad for nerve ligated rats. Skin temperature will rise to 47° C. within 5 s. The same test will be repeated four times with a 10 min wait between trails. A maximum cutoff time is set at 20 sec to avoid tissue damage. The withdrawal latencies of the four trials will be averaged. Evoked mechanical allodynia was assessed by responses to a low strength (2 g) von Frey filament stimulation using a response score system described by Vos et al. (13). The strength of the filament was well below the threshold filament strength (~12 g) that evokes withdrawals in normal rats. The same test was repeated four times with a 10 min wait between tests and the score of the four trials were averaged.

After behavioral tests, DRGs or TGs were isolated and δ-opioid receptors expression was studied using immunohistochemisty or Western blotting analyses.

Results

Figures 9A, 9B:
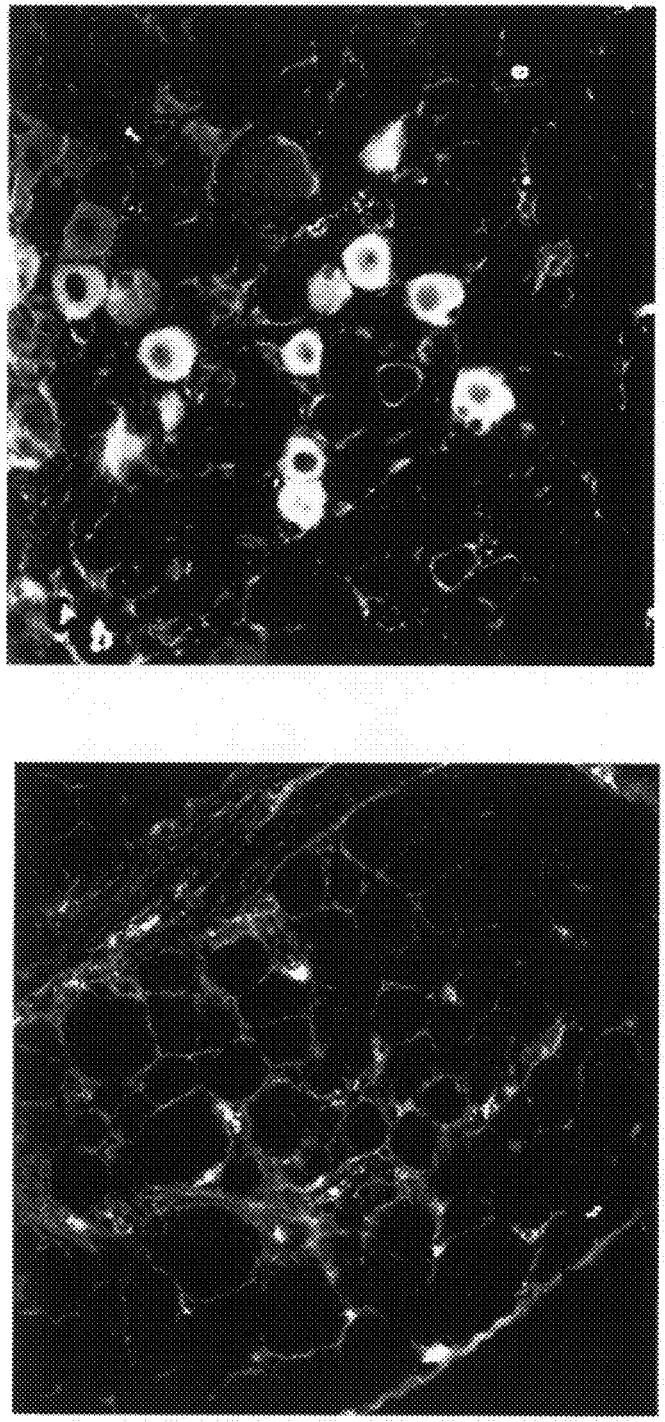
FIGS. 9A-9B shows expression of exogenous δ-opioid receptors in DRG neurons. The δ-opioid receptor gene was tagged with a FLAG motif at its N-terminal so that exogenously expressed d-opioid receptor could be monitored. FLAG labels in DRGs from rats without any treatment (FIG. 9A) and from rats injected with δ-opioid receptor-FLAG DNA (FIG. 9B) were determined. No FLAG label was found in DRG neurons in control rats, but was observed in DRG neurons in δ-opioid receptor-FLAG treated rats. Bar scale=25 μm. ganglion
Figure 11:
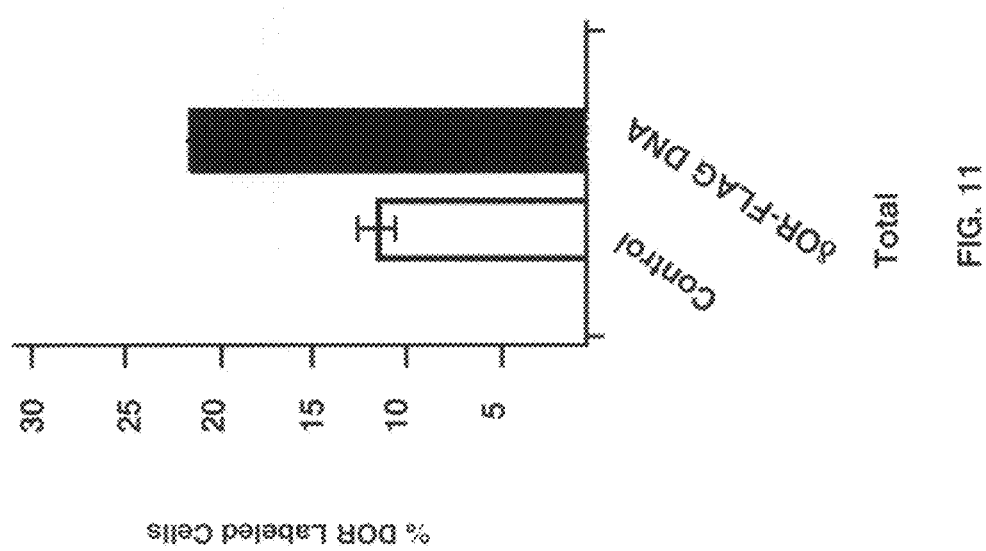
FIG. 11 shows the percentage (%) of DRG neurons expressed d-opioid receptors is significantly higher in DRGs isolated from dOR-FLAG DNA treated rats than those isolated from control rats.
Figure 12A:
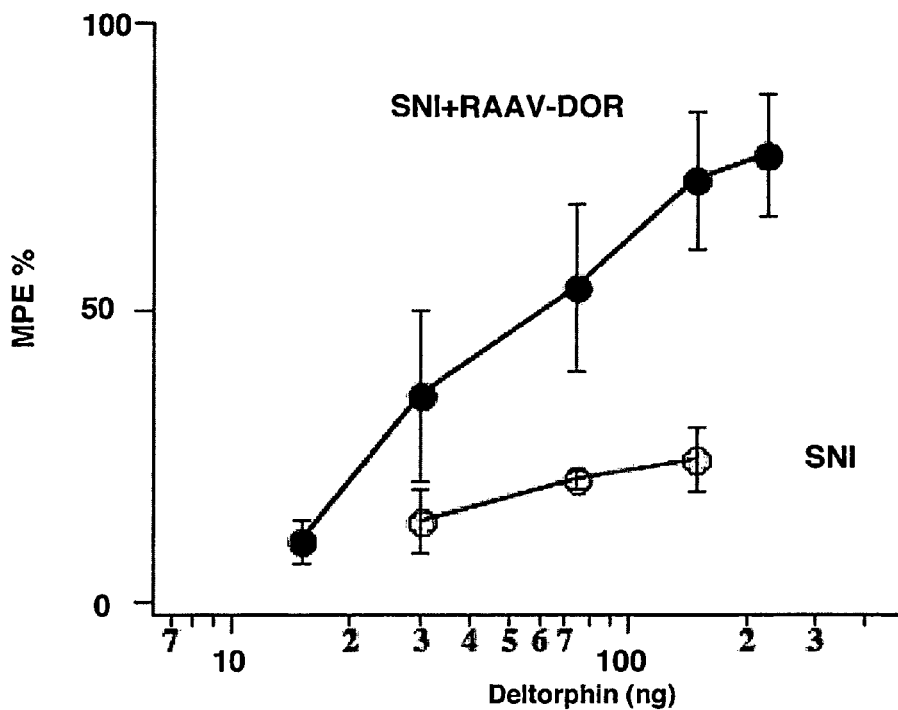
FIG. 12A-12B shows the efficacy of the d-opioid receptor agonist, deltorphin, increases following rAAV-δOR treatment.
Figure 12B:
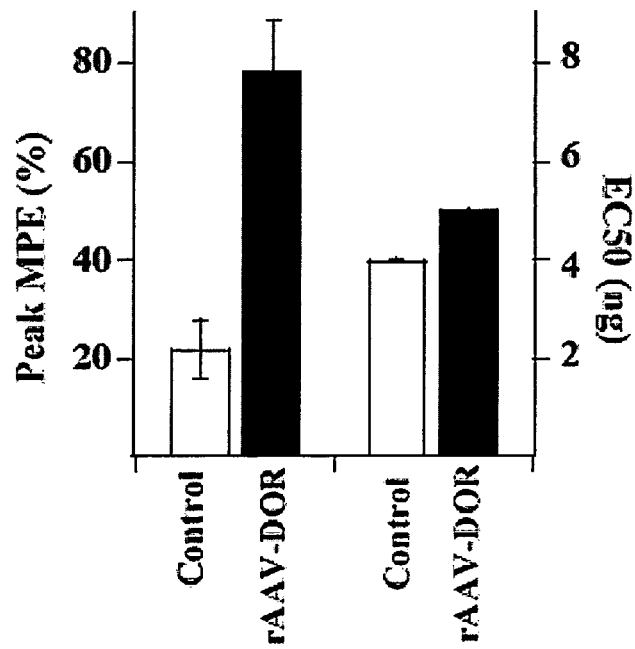
Figure 13A:
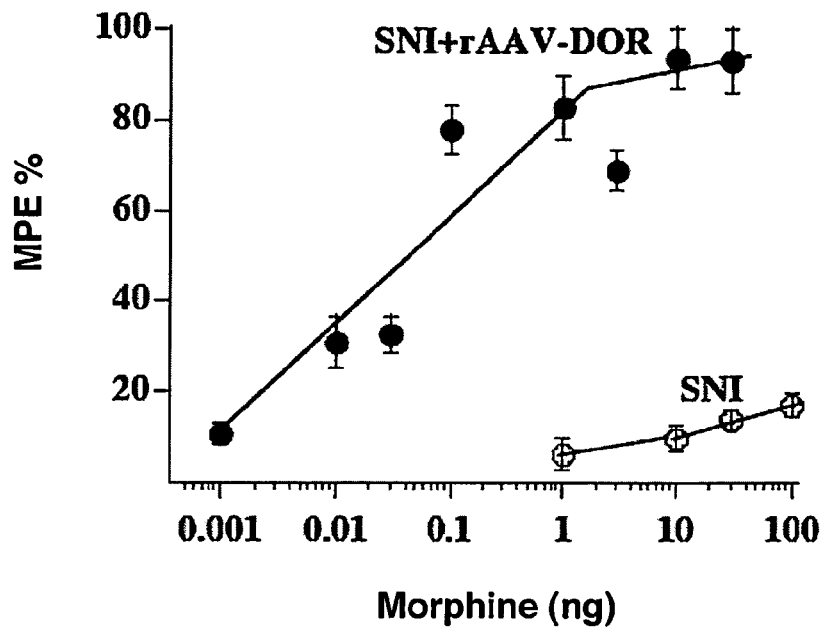
FIGS. 13A-13B shows both the potency and efficacy of intrathecal morphine to reduce allodynic responses are greatly enhanced in rAAV-dOR treated rats.
Figure 13B:
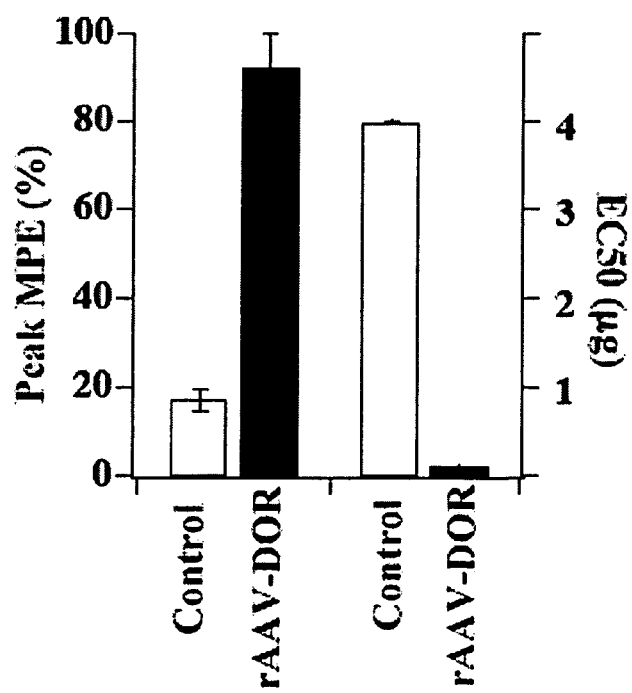
Figures 14A, 14B:
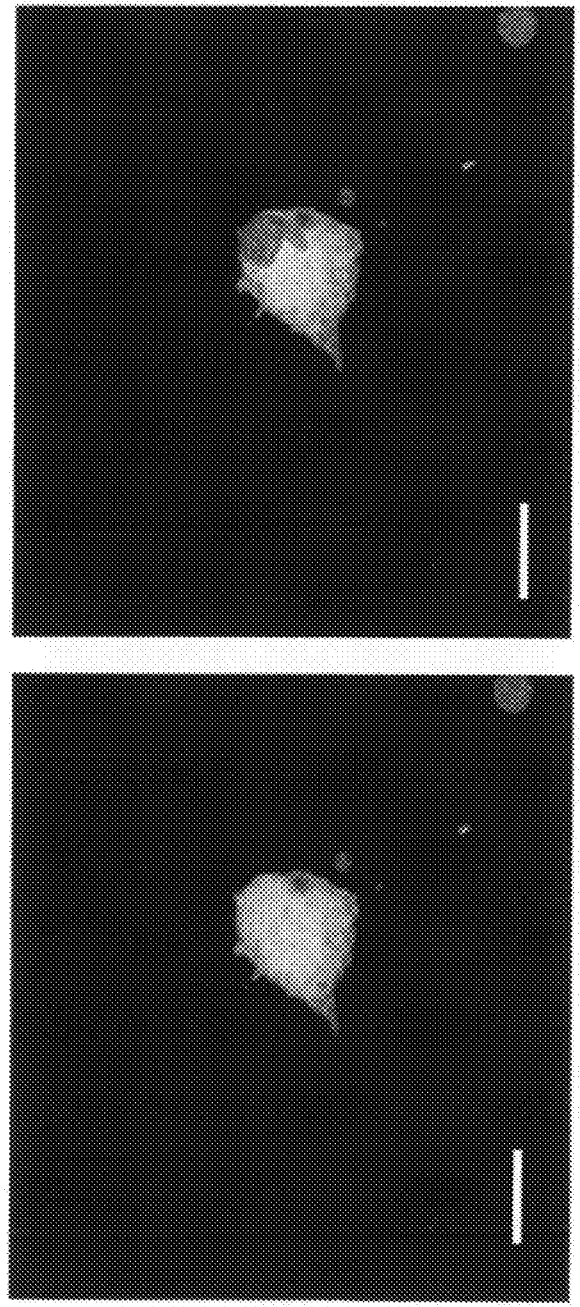
FIGS. 14A-14B show the expression of exogenous δ-opioid receptors in trigeminal cells. GFP or FLAG (labels were found in trigeminal cells treated with rAAV-dOR.

The δ-opioid receptors gene was tagged with a FLAG motif at its N-terminal so that exogenously expressed δ-opioid receptors could be monitored (FIG. 9A-9B). No FLAG label was found in DRG neurons in control rats, but was observed in δ-opioid receptor-FLAG treated rats. All of the FLAG-labeled DRG neurons were δ-opioid receptor-positive as shown in FIGS. 10A-10C. Significantly more DRG neurons expressed δORs following δOR-FLAG DNA treatment (FIG. 11) Exogenous d-opioid receptors were mostly expressed in the small DRG neurons (FIG. 9B). The efficacy of the deltorphin for allodynic behavioral responses was tested (FIGS. 12A-12B). Deltorphin was ineffective in changing allodynic responses in SNI rats but became effective in rAAV-dOR treated rats. While the efficacy increased by several folds, the potent did not change significantly. However, both potency and efficacy of morphine increased in rAAV-δOR treated rats (FIGS. 13A-13B). When the expression of δORs in trigeminal cells was assessed, it was found that δOR expression was also enhanced (FIGS. 14A-14B) and the potency and efficacy of morphine were increased, similar to those observed in DRGs.

The following references are cited herein.
1. Kabli and Cahill, Pain, 127:84-93 (2007).
2. Wu et al. Gene Ther., 9(4):245-255 (2002).
3. Thompson et al. Neuron, 11(5):903-913 (1993).
4. Wu et al., J. Virol., 72(3):2224-2232 (1998).
5. Huang et al. Neuron, 17(1):135-45 (1996).
6. Sambrook et al., pp. 18.60-18.75, in Nolan ed., Detection and Analysis of Proteins Expressed from Cloned Genes, Vol. 3, Plainview, N.Y.: Cold Spring Harbor Laboratory Press (1998).
7. Hargreaves et al. Pain, 32(1):77-88 (1988).
8. Xu et al., J. Neurosci. 22(1):93-102 (2002).
9. Willis et al. Dorsal Root Ganglion Cells and Their Processes, New York: Plenum, pp. 47-78 (1991).
10. Shaw et al. Eur. J. Cell Biol., 42(1):1-9 (1986).
11. Garcia-Anoveros et al. J. Neurosci., 15; 21(8):2678-86 (2001).
12. Chaplan et al. J Neurosci Methods 53:55-63 (1994).
13. Vos et al. J. Neurosci 14:2708-2723 (1994).

Any patents or publications mentioned in this specification are indicative of the levels of those skilled in the art to which the invention pertains. Further, these patents and publications are incorporated by reference herein to the same extent as if each individual publication was specifically and individually incorporated by reference.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of treating pain in a subject, said method comprising:
    administering a recombinant nucleic acid encoding a δ-opioid receptor operatively coupled to a promoter to a dorsal root ganglion or sciatic nerve in a subject having neuropathic or chronic pain, wherein the opioid receptor is expressed in the dorsal root ganglia; and
    administering an opioid to the subject.
2. The method of claim 1, wherein the opioid is morphine.

* * * * *